(12) United States Patent
Tripp et al.

(10) Patent No.: US 8,241,674 B2
(45) Date of Patent: Aug. 14, 2012

(54) METHODS AND COMPOSITIONS FOR HEAVY METAL DETOXIFICATION

(75) Inventors: Matthew L. Tripp, Gig Harbor, WA (US); Veera Konda, Gig Harbor, WA (US); Amy Hall, Gig Harbor, WA (US); Anu Desai, Gig Harbor, WA (US); Jeffrey S. Bland, Fox Island, WA (US)

(73) Assignee: Metaproteomics, LLC, San Clemente, CA (US)

(*) Notice: Subject to any disclaimer, the term of this patent is extended or adjusted under 35 U.S.C. 154(b) by 317 days.

(21) Appl. No.: 12/030,335

(22) Filed: Feb. 13, 2008

(65) Prior Publication Data
US 2009/0155382 A1    Jun. 18, 2009

Related U.S. Application Data

(60) Provisional application No. 60/917,425, filed on May 11, 2007.

(51) Int. Cl.
*A61K 33/30* (2006.01)
*A61P 43/00* (2006.01)

(52) U.S. Cl. ........ 424/641; 514/823; 514/423; 514/18.7; 424/756; 424/725; 424/750

(58) Field of Classification Search .................. None
See application file for complete search history.

(56) References Cited

U.S. PATENT DOCUMENTS

| | | |
|---|---|---|
| 3,451,821 A | 6/1969 | Todd et al. |
| 3,536,495 A | 10/1970 | Westermann et al. |
| 3,552,975 A | 1/1971 | Worden |
| 3,720,517 A | 3/1973 | Bavisotto et al. |
| 3,932,603 A | 1/1976 | Haas |
| 3,933,919 A | 1/1976 | Wilkinson |
| 3,965,188 A | 6/1976 | Westermann et al. |
| 4,123,561 A | 10/1978 | Grant |
| 4,133,903 A | 1/1979 | Thiele et al. |
| 4,148,873 A | 4/1979 | Owades |
| 4,154,865 A | 5/1979 | Grant |
| 4,170,638 A | 10/1979 | Owades |
| 4,389,421 A | 6/1983 | Palamand |
| 4,401,684 A | 8/1983 | Versluys |

(Continued)

FOREIGN PATENT DOCUMENTS

CN          1203268         12/1998

(Continued)

OTHER PUBLICATIONS

Dinkova-Kostova et al., Potency of Michael Reaction Acceptors as Inducers of Enzymes that Protect against Carcinogenesis Depends on their Reactivity with Sulfhydryl Groups, 2001, Proc. Natl. Acad. Sci., USA, vol. 98, pp. 3404-3409.*

(Continued)

*Primary Examiner* — Ernst Arnold
*Assistant Examiner* — Hong Yu
(74) *Attorney, Agent, or Firm* — McDermott Will & Emery LLP

(57) ABSTRACT

Compositions and methods for enhancing heavy metal detoxification are described. The compositions and methods described provide enhanced activity of key detoxification systems including that the induction of phase II detoxification enzymes, such as glutathione S-transferases (GSTs), and NADPH quinone reductase (NQO1) activity.

12 Claims, 8 Drawing Sheets

U.S. PATENT DOCUMENTS

| | | |
|---|---|---|
| 4,473,551 A | 9/1984 | Schinitsky |
| 4,554,170 A | 11/1985 | Panzer et al. |
| 4,590,296 A | 5/1986 | Cowles et al. |
| 4,644,084 A | 2/1987 | Cowles et al. |
| 4,692,280 A | 9/1987 | Spinelli |
| 4,758,445 A | 7/1988 | Klusters |
| 4,767,640 A | 8/1988 | Goldstein et al. |
| 4,857,554 A | 8/1989 | Kallimanis |
| 5,006,337 A | 4/1991 | Motitschke et al. |
| 5,013,571 A | 5/1991 | Hay |
| 5,041,300 A | 8/1991 | Todd et al. |
| 5,073,396 A | 12/1991 | Todd, Jr. |
| 5,082,975 A | 1/1992 | Todd, Jr. et al. |
| 5,155,276 A | 10/1992 | Paul |
| 5,166,449 A | 11/1992 | Todd, Jr. et al. |
| 5,264,236 A | 11/1993 | Ogasahara et al. |
| 5,286,506 A | 2/1994 | Millis et al. |
| 5,296,637 A | 3/1994 | Stegink et al. |
| 5,370,863 A | 12/1994 | Barney et al. |
| 5,387,425 A | 2/1995 | Hsu et al. |
| 5,604,263 A | 2/1997 | Tobe et al. |
| 5,641,517 A | 6/1997 | Eskeland et al. |
| 5,827,895 A | 10/1998 | Nutter et al. |
| 5,866,162 A | 2/1999 | Grattan |
| 5,902,816 A * | 5/1999 | Viner ............ 514/334 |
| 5,919,813 A | 7/1999 | de Juan |
| 5,968,539 A | 10/1999 | Beerse et al. |
| 6,020,019 A | 2/2000 | Ting et al. |
| 6,129,907 A | 10/2000 | Sreenivasan et al. |
| 6,200,594 B1 | 3/2001 | Ernest et al. |
| 6,210,701 B1 | 4/2001 | Darland et al. |
| 6,224,871 B1 | 5/2001 | Hastings et al. |
| 6,264,995 B1 | 7/2001 | Newmark et al. |
| 6,291,483 B1 | 9/2001 | Upadhyay et al. |
| 6,383,527 B1 | 5/2002 | Artman et al. |
| 6,391,346 B1 | 5/2002 | Newmark et al. |
| 6,440,465 B1 | 8/2002 | Meisner |
| 6,447,762 B1 | 9/2002 | Calcerá |
| 6,482,456 B1 | 11/2002 | Yokoo et al. |
| 6,492,429 B1 | 12/2002 | Graus et al. |
| 6,583,322 B1 | 6/2003 | Shalai et al. |
| 6,689,388 B2 | 2/2004 | Kuhrts |
| 6,790,459 B1 | 9/2004 | Cheng et al. |
| 6,801,860 B1 | 10/2004 | Dessen et al. |
| 7,078,062 B2 | 7/2006 | Hass |
| 7,144,590 B2 | 12/2006 | Khurts |
| 7,195,785 B2 | 3/2007 | Babish et al. |
| 7,205,151 B2 | 4/2007 | Babish et al. |
| 7,270,835 B2 | 9/2007 | Tripp et al. |
| 7,279,185 B2 | 10/2007 | Babish et al. |
| 7,332,185 B2 | 2/2008 | Babish et al. |
| 7,431,948 B2 | 10/2008 | Tripp et al. |
| 2002/0028852 A1 | 3/2002 | Ghai et al. |
| 2002/0076452 A1 | 6/2002 | Babish et al. |
| 2002/0077299 A1 | 6/2002 | Babish et al. |
| 2002/0086062 A1 | 7/2002 | Kuhrts |
| 2002/0086070 A1 | 7/2002 | Kuhrts |
| 2002/0156087 A1 | 10/2002 | Nuss et al. |
| 2003/0003212 A1 | 1/2003 | Chien et al. |
| 2003/0008021 A1 | 1/2003 | Babish et al. |
| 2003/0035851 A1 | 2/2003 | Chen |
| 2003/0077313 A1 | 4/2003 | Schwartz et al. |
| 2003/0096027 A1 | 5/2003 | Babish et al. |
| 2003/0113393 A1 | 6/2003 | Babish et al. |
| 2003/0133958 A1 | 7/2003 | Kuno et al. |
| 2003/0180402 A1 | 9/2003 | Jia et al. |
| 2003/0228369 A1 | 12/2003 | Kuhrts |
| 2004/0072900 A1 | 4/2004 | Artman et al. |
| 2004/0086580 A1 | 5/2004 | Tripp et al. |
| 2004/0115290 A1 | 6/2004 | Tripp et al. |
| 2004/0137096 A1 | 7/2004 | Kuhrts |
| 2004/0151792 A1 | 8/2004 | Tripp et al. |
| 2004/0219240 A1 | 11/2004 | Babish et al. |
| 2005/0042317 A1 | 2/2005 | Babish et al. |
| 2005/0129791 A1 | 6/2005 | Babish et al. |
| 2005/0191375 A1 | 9/2005 | Babish et al. |
| 2005/0192356 A1 | 9/2005 | Babish et al. |
| 2006/0074052 A1 | 4/2006 | Eliaz |
| 2006/0127511 A1 | 6/2006 | Tripp et al. |
| 2006/0127512 A1 | 6/2006 | Tripp et al. |
| 2006/0127513 A1 | 6/2006 | Tripp et al. |
| 2006/0127514 A1 | 6/2006 | Tripp et al. |
| 2006/0127515 A1 | 6/2006 | Tripp et al. |
| 2006/0127516 A1 | 6/2006 | Tripp et al. |
| 2006/0127517 A1 | 6/2006 | Tripp et al. |
| 2006/0193933 A1 | 8/2006 | Tripp et al. |
| 2006/0233902 A1 | 10/2006 | Yajima et al. |
| 2007/0003646 A1 | 1/2007 | Kuhrts |
| 2007/0020352 A1 | 1/2007 | Tripp et al. |
| 2007/0065456 A1 | 3/2007 | Woods |
| 2007/0154576 A1 | 7/2007 | Tripp et al. |
| 2007/0160692 A1 | 7/2007 | Tripp et al. |
| 2007/0166418 A1 | 7/2007 | Tripp et al. |
| 2007/0172532 A1 | 7/2007 | Babish et al. |
| 2007/0184133 A1 | 8/2007 | Tripp et al. |
| 2008/0127720 A1 | 6/2008 | Pauli et al. |
| 2008/0248131 A1 | 10/2008 | Tripp et al. |
| 2009/0118373 A1 | 5/2009 | Tripp et al. |

FOREIGN PATENT DOCUMENTS

| | | |
|---|---|---|
| DE | 1901277 | 8/1970 |
| DE | 2212148 | 9/1972 |
| DE | 3931147 | 3/1991 |
| DE | 19841615 | 3/2000 |
| EP | 0229022 | 7/1987 |
| EP | 0606599 A1 | 7/1994 |
| EP | 0681029 A2 | 11/1995 |
| EP | 1481671 | 12/2004 |
| EP | 1543834 | 6/2005 |
| EP | 1 938 828 | 7/2008 |
| GB | 2330076 | 4/1999 |
| JP | 52145509 | 12/1977 |
| JP | 58009084 | 2/1983 |
| JP | 59059623 | 4/1984 |
| JP | 363211219 | 9/1988 |
| JP | 04202138 | 7/1992 |
| JP | 6312924 | 11/1994 |
| JP | 07165583 | 6/1995 |
| JP | 07194351 | 8/1995 |
| JP | 08073369 | 3/1996 |
| JP | 8073369 | 3/1996 |
| JP | 9067245 | 3/1997 |
| JP | 09502202 | 3/1997 |
| JP | 410025247 | 1/1998 |
| JP | 10152428 | 6/1998 |
| JP | 10179129 | 7/1998 |
| JP | 11246399 | 9/1999 |
| JP | 11513037 | 11/1999 |
| JP | 11335231 | 12/1999 |
| JP | 2001161338 | 6/2001 |
| JP | 2002-12550 | 1/2002 |
| JP | 2002-505296 | 2/2002 |
| RU | 2045955 | 10/1995 |
| SU | 1247011 | 7/1986 |
| WO | WO 95007079 | 3/1995 |
| WO | WO 97/31630 | 9/1997 |
| WO | WO 97049405 | 12/1997 |
| WO | WO 99/44623 | 9/1999 |
| WO | WO 99/61038 | 12/1999 |
| WO | WO 00/68356 | 11/2000 |
| WO | WO 00/74696 | 12/2000 |
| WO | WO 02/02582 | 1/2002 |
| WO | WO 02/32234 | 4/2002 |
| WO | WO 2003/000185 | 1/2003 |
| WO | WO 03/035007 | 5/2003 |
| WO | WO 03/068205 | 8/2003 |
| WO | WO 03/075943 | 9/2003 |
| WO | WO 03/082249 | 10/2003 |
| WO | 2004037180 | 5/2004 |
| WO | WO 2004/037180 | 5/2004 |
| WO | WO 2004/062611 | 7/2004 |
| WO | WO 2005/039483 | 5/2005 |
| WO | WO 2005/084230 | 9/2005 |
| WO | WO 2006/053249 | 5/2006 |
| WO | WO 2006/062681 | 6/2006 |

| WO | WO 2007/021694 | 2/2007 |
| WO | WO 2007/067812 | 6/2007 |
| ZA | 200000857 | 8/2001 |

OTHER PUBLICATIONS

Ballatori et al., Billiary Secretion of Glutathione and of Glutathione-Metal Complexes, 1985, Fundamental and Applied Toxicology, vol. 5, pp. 816-831.*
Singh et al., Modulatory Influence of Andrographis Paniculata on Mouse Hepatic and Extraheptic Carcinogen Metabolizing Enzymes and Antioxidant Status, 2001, Phytother. Res., vol. 15, pp. 382-390.*
Chung et al., Cytotoxicity of Nitric Oxide is Alleviated by Zinc-Mediated Expression of Antioxidant Genes, 2006, Exp. Biol. Med., vol. 231, pp. 1555-1563.*
Dinkova-Kostova et al., Potency of Michael Reaction Acceptors as Inducers of Enzymes that Protect against Carcinogenesis Depends on their Reactivity with Sulfhydryl Groups, 2001, Proc. Natl. Acad. Sci., USA, vol. 98, pp. 3404-3409, Abstract, Table 1, compound 21.
Ballatori et al, Biliary Secretion of Glutathione and of Glutathione-Metal Complexes, 1985, Fundamental and Applied Toxicology, vol. 5, pp. 816-831, Abstract.
Sing, et al., Modulatory Influence of Andrographis Paniculata on Mouse Hepatic and Extrahepatic Carcinogen Metabolizing Enzymes and Antioxidant Status, 2001, Phytother. Res., vol. 15, pp. 382-390 Abstract.
Chung et al. Cytotoxicity of Nitric Oxide Is Alleviated by Zinc-Mediated Expression of Antioxidant Genes, 2006, Exp Biol Med, vol. 231, pp. 1555-1563, Introduction,para 2.
International Search Report for corresponding PCT Application No. PCT/US08/53803, 2 pp.
Written Opinion for corresponding PCT Application No. PCT/US08/53803, 5 pp.
International Search Report for related PCT Application No. PCT/US08/53579, 2 pp.
Written Opinion for related PCT Application No. PCT/US08/53579, 5 pp.
Abel-salam et al., Pharmacological Research, England 47(4), pp. 311-340 (Apr. 2003).
Albal, MV., et al., "Clinical evaluation of berberine in mycotic infections." Indian J. Ophthalmol 34:91-2 (1986).
Anto, et al., "Anti-inflammatory Activity of Natural and Synthetic Curcuminoids", Pharmacy and Pharmacology Communications, 4(2), pp. 103-106 (1998).
Baldermann et al., J. Chromatography a 1192(1):191-3 (May 23, 2008) (Epub Apr. 8, 2008); abstract only (1 page).
Bermejo, et al. Rev. Esp. Enferm. Dig. 95(9): 621-624 and 625-628 (2003).
Bolick D et al., Endocrinology 144(12), pp. 5227-5231 (Dec. 2003).
Brown, et al. J. Chem. Soc. 545 (1959).
Buhler et al., Antioxidant Activities of Flavanoids, 3 pages, Nov. 2000.
Byrne, et al. J. Chem. Soc. (C):2810 (1971).
Carroccio, et al. Clin. Chem. 49(6):861-867 (2003).
Carson, J. Am. Chem. Soc. 73:1850-1851 (1951).
Chandra, et al. Indian J. Medical Research 60(1):138-142 (1972).
Charlier, et al. Eur. J. Med. Chem. 38:645-659 (2003).
Chattopadhyay et al., Current Science, 87(1) (Jul. 10, 2004).
Chen Wei-Jen et al., Journal of Agricultural and Food Chemistry 52(1), pp. 55-64 (Jan. 01, 2004).
Chou et al. Eur. J. Biochem. 115:207-216 (1981).
Chou, et al. Adv enzyme regul 22:27-55 (1983).
Chou, et al. Eur. J. Biochem. 115:207-216 (1981).
Chou, et al. J. Biol. Chem. 252(18):6438-6442 (1977).
Chou, et al. J. Theor. Biol. 35:285-297 (1972).
Chou, J. Theor. Biol. 59:253-276 (1976).
Chou, et al., Tips, pp. 450-454, Nov. 1983.
Cohen, Protein Kinases—the major drug targets of the twenty-first century? Nature Reviews, 1: 309-315 (2002).
Costa, et al. Digest. Liver Dis. 35:642-647 (2003).
Davies, WL. Abstract—Fertiliser, Feeding Stuffs and Farm Supplies J. 11:694 (1926).

De Keukeleire "Fundamentals of Beer and Hop Chemistry" Quimica Nova, 23(1) pp. 108-112 (2000).
Ding, et al. Biochem. Biophys. Res. Comm. 261:218-223 (1999).
European Examination Report for EP App. No. 02748188.6-1216, Apr. 28, 2011.
European Search Report for EP App. No. 07809709.4, Jan. 4, 2010.
European Search Report EP 05 723 839.6, Jan. 11, 2010.
European Search Report EP 10006768, Oct. 28, 2010.
European Search Report EP 10011254, Jan. 31, 2011.
European Search Report EP 10013109, Dec. 14, 2010.
European Search Report EP 10162893, Sep. 14, 2010.
European Search Report for corresponding EP Application No. 02737562.5 (4 pages).
European Search Report for related European Application No. 02784313.5.
Exercise as Treatment for Arthritis, Rheumatic and Immunologic Diseases, Cleveland Clinic, www.clevelandclinic.org, Mar. 14, 2000.
Extended European Search Report EP 10162893.1, Sep. 14, 2010.
Extended European Search Report EP 07717798.8, Jun. 29, 2010.
Extended European Search Report EP 07809708.6, May 1, 2010.
Foucault et al., J. Chromatography A 808(1-2):3-22 (May 29, 1998); abstract only (3 pages).
Friedman, et al. J Cutan Med. Surg. 6(5):449-459 (2002).
Gao et al., J. Food Sci. Nutr. vol. 9, pp. 240-244 (2004).
Gerhauser et al., Molecular Cancer Therapeutics vol. 1, No. 11, pp. 959-969 (2002).
Gerhauser, Beer Constituents as Potential Cancer Chemopreventive Agents, EP Journal of Cancer 41; 1941-1954: (2005).
Germany, "The Absolutely German Drink," contents of beer, 2004, 5 pages.
Gilani, "Studies on Antihypertensive and Antispasmodic Activities of Methanol Extract of Acacia nilotica Pods", Phytotherapy Research 13: 665-669 (1999).
Goldstein, et al. Am. J. Gastroenterol. 96(4):1019-1027 (2001).
Halter, et al. Gut 49:443-453 (2001).
Hamberg, et al. J. Bio. Chem. 246(22):6713-6721 (1971).
Hariddradilepah 01, TKDL, Aug. 1, 1999, XP003024376, (3 pages).
Huang, et al. Cancer Res. 51:813-819 (1991).
Information on ArthroTrimTM product, downloaded from Internet, Aug. 30, 2002.
Information on "Hops and Beer Flavours", IOB Technical Symposium, Apr. 2001, pp. 1-9.
Information on "Zyflamend and Zyflamend PM", downloaded from Internet, Aug. 30, 2002.
International Search Report for Corresponding PCT Application No. PCT/US05/41018; 2pp, May 30, 2008.
International Search Report for PCT /US06/30920, Aug. 3, 2007, 3 pages.
International Search Report for PCT/US02/19617, Jun. 17, 2003.
International Search Report for PCT/US04/16043, Jul. 27, 2005.
International Search Report for PCT/US06/47196, Dec. 20, 2007.
Jach, Przegl Dermatol. 65(4):379-381 (1978).
Jafri et al., Pakistan Journal of Science, vol. 61, No. 4, pp. 220-222 (Dec. 2009).
Kaltner, Investigation of formation of Hops Aroma and technological Measures for Products of Hops-Aromatic Beers, Technical University of Munich, 7 pp. corresponding to Kaltner, D., Technische Universitat Munchen, (Nov. 30, 2000), pp. 1-193, plus Tabs. AH1-AH31.
Kanematsu, et al. J Bone Miner Res 12(11):1789-1796 (1997).
Konda, et al., Arthritis & Rheumatism 62(6): 1683-1692, (2010).
Kuo et al., Cancer Letter, 203:127-137 (2004).
Lamy Virginie et al., Apoptosis, an Int'l Journal on Programmed Cell Death,13(10), pp. 1232-1242 (Aug. 25, 2008).
Lamy Virginie et al., Carcinogenesis, 28(7), pp. 1575-1581 (Jul. 2007).
Lerman et al, FASEB Journal, Fed. of American Soc. For Experimental Biol., vol. 18, No. 4-5 (Jan. 1, 2004).
Lopes, Curr. Med Res Opin. 8(3):145-149 (1982).
Lukaczer et al., Phytotherapy Research, vol. 19, No. 10, pp:864-869 (2005).
Mannering et al., Food, Nutrition and Chemical Toxicity X(X), pp. 311-323 (Jan. 1, 1993).

Meling, et al. Scand. J. Gastroenterol. 31:339-344 (1996).
Minich et al., Journal of nutrition and Metabolism, vol. 2010, article ID 467316, pp. 1-11, (2010).
Murvadyaghrtam, TKDL, Jan. 1, 2001, XP003024377 (4 pages).
Murvadyaghrtam, TKDL, Jan. 1, 1990, XP003024379 (4 pages).
Newark, et al., "Beyond Aspirin", pp. 147-151, Hohm Press (2000).
Noreen, et al. J. Nat. Prod 61:2-7 (1998).
Office Action issued for U.S. Appl. No. 11/667,614 mailed Apr. 16, 2010.
Office Action issued for U.S. Appl. No. 11/667,615 mailed Mar. 16, 2010.
Office Action issued for U.S. Appl. No. 11/701,583 mailed Feb. 8, 2008.
Office Action issued for U.S. Appl. No. 11/701,583 mailed Jul. 6, 2009.
Office Action issued for U.S. Appl. No. 11/701,583 mailed Nov. 26, 2008.
Office Action issued in U.S. Appl. No. 10/464,834 on Aug. 3, 2010.
Office Action issued in U.S. Appl. No. 10/532,388 on Mar. 26, 2010.
Office Action issued in U.S. Appl. No. 10/532,388 on Jun. 28, 2011.
Office Action issued in U.S. Appl. No. 10/590,301 on Aug. 19, 2010.
Office Action issued in U.S. Appl. No. 10/590,424 on Jun. 29, 2010.
Office Action issued in U.S. Appl. No. 10/789,814 on Jun. 11, 2010.
Office Action issued in U.S. Appl. No. 10/789,814 on Mar. 18, 2011.
Office Action issued in U.S. Appl. No. 11/344,555 on Jan. 19, 2011.
Office Action issued in U.S. Appl. No. 11/344,556 on Sep. 3, 2010.
Office Action issued in U.S. Appl. No. 11/344,556 on Dec. 16, 2009.
Office Action issued in U.S. Appl. No. 11/344,556 on Mar. 27, 2009.
Office Action issued in U.S. Appl. No. 11/344,557 on Mar. 25, 2010.
Office Action issued in U.S. Appl. No. 11/344,557 on Apr. 21, 2008.
Office Action issued in U.S. Appl. No. 11/344,557 on Aug. 28, 2009.
Office Action issued in U.S. Appl. No. 11/344,557 on Jan. 10, 2007.
Office Action issued in U.S. Appl. No. 11/344,557 on Sep. 26, 2007.
Office Action issued in U.S. Appl. No. 11/636,867 on Aug. 30, 2010.
Office Action issued in U.S. Appl. No. 11/636,867 on Mar. 08, 2011.
Office Action issued in U.S. Appl. No. 11/649,584 on Mar. 3, 2010.
Office Action issued in U.S. Appl. No. 11/344,552 on Sep. 8, 2010.
Office Action issued in U.S. Appl. No. 11/501,393 on Aug. 25, 2010.
Office Action issued in U.S. Appl. No. 11/729,696 on Nov. 1, 2010.
Office Action issued in U.S. Appl. No. 11/820,600 on Sep. 30, 2010.
Office Action issued in U.S. Appl. No. 11/820,607 on Oct. 12, 2010.
Office Action issued in U.S. Appl. No. 12/030,335 on Oct. 21, 2010.
Office Action issued in U.S. Appl. No. 12/048,613 on Dec. 8, 2010.
Office Action issued in U.S. Appl. No. 12/754,820 on Mar. 15, 2011.
Office Action issued in U.S. Appl. No. 12/626,392 on Oct. 27, 2010.
Office Action issued in U.S. Appl. No. 11/729,696 on Mar. 25, 2010.
Office Action issued in U.S. Appl. No. 11/729,696 on Jul. 14, 2011.
Office Action issued in U.S. Appl. No. 11/820,755 on Oct. 18, 2010.
Office Action issued in U.S. Appl. No. 11/820,755 on Jun. 1, 2011.
Office Action issued in U.S. Appl. No. 10/464,410 on May 23, 2011.
Office Action issued in U.S. Appl. No. 11/820,607 on May 23, 2011.
Office Action issued in U.S. Appl. No. 11/820,653 on Aug. 8, 2011.
Office Action issued in U.S. Appl. No. 11/820,600 on May 26, 2011.
Office Action issued in U.S. Appl. No. 10/532,388 on Oct. 1, 2010.
Office Action issued in U.S. Appl. No. 11/501,393 on Nov. 9, 2011.
Office Action issued in U.S. Appl. No. 11/636,867 on Oct. 28, 2011.
Office Action issued in U.S. Appl. No. 12/626,392 on Jul. 8, 2011.
Office Action issued in U.S. Appl. No. 12/331,887 on Oct. 12, 2011.
Office Action issued in U.S. Appl. No. 12/754,820 on Nov. 30, 2011.
Ohkura et al., Japanese Joural of Pharmacognosy, 44(3):171-175, (1990).
Pairet, et al. Inflamm. Res 47, Supplement 2S93-S101 (1998).
Panglisch, Monafsschrift fuer Brauwissen Schaft, 43(1), 4-16 (1990).
Parmar et al., Phytochemistry, vol. 28(2):591-593 (1989).
Parts per Milliion, 1 page, 2004.
Pippa, et al. Scand. J. Gastroenterol. Suppl. 167:32-35 (1989).
Plewig, et al. J Invest. Dermatol. 65(6):532-536 (1975).
Poullis ,et al. J. Gastroenterol. Hepatol. 18:756-762 (2003).
Provital Group, Rosemary-eco Botany, 2007, 9 pages.
Q & A, (what does ppm or ppb mean?) 3 pages, 2004.
Rahman, M.M., et al., "Conjugated linoleic acid inhibits osteoclast differentiation of RAW264.7 cells by modulating RANKL signaling" J. Lipid Res., 47(8): 1739-1748, (2006).
Ringbom, et al. J. Nat Prod 61:1212-1215 (1998).
Røseth, Digest. Liver Dis. 35:607-609 (2003).
Schjerven, et al. Br. J. Dermatol. 149:484-491 (2003).
Schmalreck et al, Canadian Journal of Microbiology, vol. 21:205-212 (1975).
Shah, et al. Gut 48:339-346 (2001).
Shimamura, et al. Biochem. Biophys. Res. Comm. 289:220-224 (2001).
Shureiqi, et al. Cancer Res. 61:6307-6312 (2001).
Sivri, Fundam. Clinic. Pharmacol. 18:23-31 (2004).
Smith, et al., Natural Foam Stabilizing and Bittering Compounds Derived From Hops, Journal of the American Society of Brewing Chemists, vol. 56, No. 2, 1998, pp. 52-57.
Stephan T E et al., Biochemical Pharmacology, 55(4), pp. 505-514, (Feb. 15, 1998).
Stevens, Xanthohumol and related Prenylflavonoids from Hops and Beer: to Your Good Health, Science Direct, 2pp (2004).
Subbaramaiah, et al. Cancer Res. 60:2399-2404 (2000).
Suh, et al. Cancer Res 58:717-723 (1988).
Supplemental European Search Report for EP 07845228, Jan. 18, 2010.
Supplementary European Search Report form related EP Application No. 05851567, 8PP, Apr. 28, 2008.
Supplementary Partial European Search Report for related European Patent Application No. 05723895.8, 5 pages. (2007).
Supplementary European Search Report for EP Application No. EP 08729724, 9PP, Apr. 14, 2011.
Supplementary European Search Report for EP Application No. EP 08859091, 5PP, Jan. 28, 2011.
Tagashira M et al., Bioscience, Biotechnology, and Biochemistry, 59(4), pp. 740-742 (Apr. 1995).
The national. 3 pages (1999).
Tibble, et al. Drugs Today 37(2):85-96 (2001).
Tibble, et al. Gut 45:362-366 (1999).
Tiktakaghrtam, TKDL, Jan. 1, 1922, XP003024378 (1922).
Tobe, et al. Biosci. Biotech. Biochem 61(1):158-159 (1997).
Turmeric: The Ayurvedic Spice of Life, published at www.bioponic.com/pdfs/TurmericAyurveda.pdf (2003).
US News and world report re Palliative Care, 10 pages (2008).
Van Montfrans et al. Inflammatory Signal Transduction in Crohn's Disease and Novel Therapeutic Approaches. Science Direct, Jun. 2, 2002, 20 pages. Biochemical Pharmacology, vol. 64, issues 5-6.
Vanhoecke et al., In Vivo, vol. 19, No. 1, pp. 103-107 (2005).
Vanhoenacker, et al., Journal of Chromatography, vol. 1035, No. 1, (Apr. 30, 2004), pp. 53-61.
Verzele, et al. Chemistry and analysis of hop and beer bitter acids, Developments in food science, 27, pp. 44-51, 88-139 (1991).
Verzele and De Keukeleire (eds.) Chemistry and Analysis of Hop and Beer Bitter Acids; Elsevier, Chapters 5, 20 pages (1991).
Verzele and De Keukeleire (eds.) Chemistry and Analysis of Hop and Beer Bitter Acids; Elsevier, Chapters 6, 8 pages (1991).
Wang, et al. Free Radical Biology & Medicine 27:612-616 (1999).
Ward, et al., Therapeutic Potential of Phosphoinositide 3-Kinase Inhibitors, Chemistry & Biology, vol. 10, 207-210, Mar. 2003.
Warner, et al. Proc Natl Acad Sci USA 96:7563-7568 (1999).
Written Opinion for corresponding PCT Application No. PCT/US05/41018; 3 pp, May 30, 2008.
Yamamoto, et al. Abstract—Prostaglandins & Other Lipid Mediators 59:1-235 (1999).
Yamamoto, FEBS Letters 465:103-106 (2000).
Yui, et al. Biol. Pharm. Bull. 26(6):753-760 (2003).
Zhao Feng et al., Biological and Pharmaceutical Bulletin, 26(1), pp. 61-65 (Jan. 2003).

* cited by examiner

METHODS AND COMPOSITIONS FOR HEAVY METAL DETOXIFICATION

CROSS-REFERENCE TO RELATED APPLICATIONS

This patent application claims priority to U.S. provisional application Ser. No. 60/917,425 filed on May 11, 2007.

BACKGROUND OF THE INVENTION

1. Field of the Invention

The present invention relates generally to compositions and methods to promote heavy metal detoxification in mammals in need. More specifically, the invention relates to the use of spent hops, zinc, (1,7-Bis(4-hydroxy-3-methoxyphenyl)hepta-1,6-diene-3,5-dione), and (3-(2-(Decahydro-6-hydroxy-5-(hydroxymethyl)-5,8a-dimethyl-2-methylenenaphthyl)ethylidene)dihydro-4-hydroxyfuran-2(3H)-one) or combinations thereof for heavy metal detoxification in the non-acute state.

2. Description of the Related Art

There are numerous metals which may pose health concerns due to residential or occupational exposure. Of these; antimony, arsenic, bismuth, cadmium, cerium, chromium, cobalt, copper, gallium, gold, iron, lead, manganese, mercury, nickel, platinum, silver, tellurium, thallium, tin, uranium, vanadium, and zinc are considered the most problematic. Many of these elements are common to our diet and environment and are actually necessary for maintaining good health. However, exposure to larger amounts may result in acute or chronic toxicity.

Heavy metal toxicity can result in damaged or reduced mental and central nervous function, lower energy levels, and damage to blood components, lungs, kidneys, liver, and other vital organs. Furthermore, long term chronic exposure has been attributed to physical, neurological or muscular degenerative processes which appear to mimic muscular dystrophy, multiple sclerosis or Parkinson's or Alzheimer's diseases. Additionally, some heavy metals have been identified as potent mutagens and/or carcinogens.

Heavy metal toxicity symptomology is not difficult to recognize. The symptoms, usually severe, are commonly associated with a known exposure or ingestion of the metal. Onset of symptoms is usually rapid and can include cramping, nausea, and vomiting; pain; sweating; headaches; difficulty breathing; impaired cognitive, motor, and language skills; mania; and convulsions.

Symptoms of chronic exposure are very similar to symptoms of other health conditions and often develop slowly over months or even years. However, the symptoms of toxicity resulting from chronic exposure (impaired cognitive, motor, and language skills; learning difficulties; nervousness and emotional instability; and insomnia, nausea, lethargy, and feeling ill) while easily recognized are much more difficult to associate with their cause. A further problem in identifying chronic exposure occurs because the symptoms of chronic exposure may abate from time to time, leading the afflicted individual to postpone seeking treatment, believing the symptoms are related to something other than metal toxicity.

The most commonly encountered toxic metals include aluminum, arsenic, cadmium, iron, lead, and mercury. Arsenic and lead poisonings tend to be the most common due to their wide use in smelting processes, chemical and glass manufacture, or pesticide use (arsenic) while lead exposure can occur from pipes, paint, batteries, and PVC plastics. Target organs for arsenic toxicity include blood, kidneys and digestive, skin and central nervous systems while lead most commonly targets bones, brain, blood, kidneys and the thyroid.

Cadmium toxicity usually targets the brain and kidney resulting from environmental exposures from PVC pipes, batteries and paint pigments.

Aluminum, although not a "heavy" metal per se, has been associated with neurotoxicity (Halatek T, et al., J Environ Sci Health A Tox Hazard Subst Environ Eng. 43(2):118-24, 2008), Alzheimer's disease (Prolo P., et al., Bioinformation. 2007 2(1):24-7, 2007), Molloy, D W., et al., J Toxicol Environ Health A. 70(23):2011-9, 2007), and cell death (Satoh E., et al., Biol Pharm Bull. 30(8):1390-4, 2007).

Some heavy metals have been identified as potent mutagens and/or carcinogens. These metals have been implicated in apoptosis and cell growth regulation, nuclear transcription regulation and effecting various signal transduction pathways. These metals have also been identified as possessing activity effecting gene expression, carcinogenesis, mutagenesis, and cytotoxicity, as well as in free radical generation. For a review, see Wang S, and Shi X., Mol Cell Biochem 222; 3-9, 2001.

Xenobiotic metabolizing enzymes play a major role in regulating the toxic, oxidative damaging, mutagenic, and neoplastic effects of chemical carcinogens. Mounting evidence has indicated that the induction of phase II detoxification enzymes, such as glutathione S-transferases (GSTs), and NADPH quinone reductase (NQO1) activity result in protection against toxicity and chemical carcinogenesis, especially during the initiation phase. NQO1 is a flavoprotein that catalyzes two electron reduction of quinones and nitrogen oxides (Riley, R. J. and P. Workman, Biochem Pharmacol, 43(8): 1657-69, 1992 and Ross, D., et al., Cancer Metastasis Rev, 12(2): 83-101, 1993). Although the major function of this protein may be to reduce the formation of reactive oxygen species by decreasing one electron reduction and the associated redox cycling, it also plays a role in activation of some anticancer drugs and cancer prevention (Begleiter, A., et al., Cancer Lett, 45(3): 173-6, 1989 and Begleiter, A., et al., Oncol Res, 9(6-7): 371-82, 1997) Recent studies suggest that NQO1 may also be involved in regulation of the transcription factor p53 and apoptosis (Asher, G., et al., Proc Natl Acad Sci USA, 98(3): 1188-93, 2001 and Long, D. J., 2nd, et al., Cancer Res, 62(11): 3030-6, 2002).

The transcriptional activation of the phase II enzymes has been traced to a cis-acting transcriptional enhancer called ARE (Rushmore, T. H., et al., Proc Natl Acad Sci USA, 87(10): 3826-30, 1990), or alternatively, the electrophile response element (Friling, R. S., et al., Proc Natl Acad Sci USA, 87(16): 6258-62, 1990). It has been shown that the transcription factor Nrf-2 positively regulates the ARE-mediated expression of the phase II detoxification enzyme genes. Itoh et al. (Biochem Biophys Res Commun, 236(2): 313-22, 1997) have recently established by gene-targeted disruption in mice that Nrf-2 is a general regulator of the phase II enzyme genes in response to electrophiles and reactive oxygens. More recently, the general regulatory mechanism underlying the electrophile counterattack response has been demonstrated in which electrophilic agents alter the interaction of Nrf-2 with its repressor protein (Keap-1), thereby liberating Nrf-2 activity from repression by Keap-1, culminating in the induction of the phase II enzyme genes and antioxidative stress protein genes via AREs (Itoh, K., et al., Genes Dev, 13(1): 76-86, 1999).

It has been suggested that the dissociation of Nrf-2 from Keap-1 may involve modification of either one of these proteins and could be achieved by direct or indirect mechanisms. For example, Nrf-2 can be phosphorylated by components of the MAP kinase cascade (Yu, R., et al., J Biol Chem, 274(39): 27545-52, 1999), which could result in its dissociation. On the other hand, Dinkova-Kostova et al. (Dinkova-Kostova, A. T., et al., Proc Natl Acad Sci USA, 98(6): 3404-9, 2001) have provided an alternative possibility that the dissociation of this complex may be potentiated by the direct interaction of electrophilic agents with reactive thiol residues in either of the two proteins. This hypothesis is supported by the strong relationship between the potency of the agents as inducers of the gene expression through the ARE and their rate of reaction with sulfhydryl groups. This mechanism implies that the inducing agent will become covalently bound either to Keap-1 or Nrf-2.

Heme oxygenase-1 (HO-1) an essential enzyme in heme catabolism, and metallothionein IIA (MT-2A), a small metal-binding protein with clusters of cysteins, are induced in HeLa cells following the treatment with cadmium or zinc. Both proteins are considered to be involved in the defense system against metal toxicity. Heme oxygenase is regulated by both Nrf-2 and MTF-1 transcriptional factors through the activation of ARE and MRE binding sites on heme oxygenase gene.

By and large, medical research has been directed to acute instances of metal toxin exposure where detoxification and removal of the toxic substance must be accomplished rapidly insofar as the continued presence of the metal toxin places the patient in a true life or death situation. The most common detoxification treatments for metal toxicity include chemical inactivation, metabolic detoxification, or, for example, chelation.

Currently, these treatments are considered neither appropriate nor indicated for low level toxin exposures, thereby creating a pressing need for safe and effective methods to detoxify individuals with sub-acute metal toxin exposures before toxin build up reaches the requisite level necessitating the more extreme measures described above. The inventors have identified a number of compounds having a history of safety which modulate the activity of key detoxification enzymes and promote toxin removal from the body. The invention described herein teaches enhancement or inducement of detoxification enzyme systems for sub-acute toxin exposures through modulation of key detoxification enzymes and concomitant administration of additional detoxifying and nutritional agents

SUMMARY OF THE INVENTION

The present invention relates to compositions and methods to promote heavy metal detoxification under non-acute conditions in mammals. More specifically, the invention relates to the use of spent hops, zinc, (1,7-Bis(4-hydroxy-3-methoxyphenyl)hepta-1,6-diene-3,5-dione), and (3-(2-(Decahydro-6-hydroxy-5-(hydroxymethyl)-5,8a-dimethyl-2-methyl-enenaphthyl)ethylidene)dihydro-4-hydroxyfuran-2(3H)-one) or combinations thereof for heavy metal detoxification in the non-acute state.

A first embodiment of the invention describes compositions for promoting heavy metal detoxification in a mammal in need. Here the compositions comprise a therapeutically effective amount of at least two members selected from the group consisting of spent hops; 1,7-Bis(4-hydroxy-3-methoxyphenyl)hepta-1,6-diene-3,5-dione; zinc; and 3-(2-(Decahydro-6-hydroxy-5-(hydroxymethyl)-5,8a-dimethyl-2-methylenenaphthyl)ethylidene)dihydro-4-hydroxyfuran-2 (3H)-one.

Methods for promoting heavy metal detoxification in a mammal in need are described in a second embodiment. In this embodiment the methods entail administering to the mammal a composition comprising a therapeutically effective amount of at least two members selected from the group consisting of spent hops; 1,7-Bis(4-hydroxy-3-methoxyphenyl)hepta-1,6-diene-3,5-dione; zinc; and 3-(2-(Decahydro-6-hydroxy-5-(hydroxymethyl)-5,8a-dimethyl-2-methyl-enenaphthyl)ethylidene)dihydro-4-hydroxyfuran-2(3H)-one.

A further embodiment of the invention describes a composition comprising: from about 0.10 to about 10.00 grams of spent hops; from about 5 to about 1200 mg of 1,7-Bis(4-hydroxy-3-methoxyphenyl)hepta-1,6-diene-3,5-dione; from about 0.10 to about 24 mg of zinc; and from about 5 to about 1200 mg of 3-(2-(Decahydro-6-hydroxy-5-(hydroxymethyl)-5,8a-dimethyl-2-methylenenaphthyl)ethylidene)dihydro-4-hydroxyfuran-2(3H)-one.

Another embodiment describes methods for promoting heavy metal detoxification in a mammal in need. In this embodiment the method utilizes a composition comprising: from about 0.10 to about 10.00 grams of spent hops; from about 5 to about 1200 mg of 1,7-Bis(4-hydroxy-3-methoxyphenyl)hepta-1,6-diene-3,5-dione; from about 0.10 to about 24 mg of zinc; and from about 5 to about 1200 mg of 3-(2-(Decahydro-6-hydroxy-5-(hydroxymethyl)-5,8a-dimethyl-2-methylenenaphthyl)ethylidene)dihydro-4-hydroxyfuran-2 (3H)-one.

A method for promoting heavy metal detoxification in a mammal in need is described in another embodiment. Here the method comprises administering to the mammal a composition comprising a therapeutically effective amount of spent hops.

DETAILED DESCRIPTION OF THE INVENTION

Figure 1:
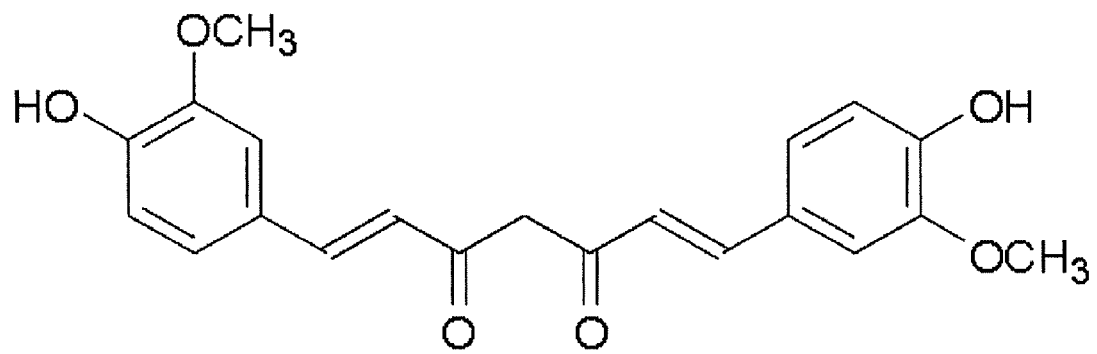
FIG. 1 is a graphic representation of the chemical structure of 1,7-Bis(4-hydroxy-3-methoxyphenyl)hepta-1,6-diene-3,5-dione.

The present invention relates to compositions and methods to promote heavy metal detoxification under non-acute conditions in mammals. More specifically, the invention relates to the use of spent hops, zinc, (1,7-Bis(4-hydroxy-3-methoxyphenyl)hepta-1,6-diene-3,5-dione), and (3-(2-(Decahydro-6-hydroxy-5-(hydroxymethyl)-5,8a-dimethyl-2-methylenenaphthyl)ethylidene)dihydro-4-hydroxyfuran-2(3H)-one) or combinations thereof for heavy metal detoxification in the non-acute state.

The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of recombinant DNA technology include Sambrook et al., Molecular Cloning: A Laboratory Manual, 2nd Ed., Cold Spring Harbor Laboratory Press, New York (1989); Kaufman et al., Eds., Handbook of Molecular and Cellular Methods in Biology in Medicine, CRC Press, Boca Raton (1995); McPherson, Ed., Directed Mutagenesis: A Practical Approach, IRL Press, Oxford (1991). Standard reference works setting forth the general principles of pharmacology include Goodman and Gilman's The Pharmacological Basis of Therapeutics, 11th Ed., McGraw Hill Companies Inc., New York (2006).

In the specification and the appended claims, the singular forms include plural referents unless the context clearly dictates otherwise. As used in this specification, the singular forms "a," "an" and "the" specifically also encompass the plural forms of the terms to which they refer, unless the content clearly dictates otherwise. Additionally, as used herein, unless specifically indicated otherwise, the word "or" is used in the "inclusive" sense of "and/or" and not the "exclusive" sense of "either/or." The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

Reference is made hereinafter in detail to specific embodiments of the invention. While the invention will be described in conjunction with these specific embodiments, it will be understood that it is not intended to limit the invention to such specific embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail, in order not to unnecessarily obscure the present invention.

Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

A first embodiment of the invention describes compositions for promoting heavy metal detoxification in a mammal in need, where the compositions comprise a therapeutically effective amount of at least two members selected from the group consisting of spent hops; 1,7-Bis(4-hydroxy-3-methoxyphenyl)hepta-1,6-diene-3,5-dione; zinc; and 3-(2-(Decahydro-6-hydroxy-5-(hydroxymethyl)-5,8a-dimethyl-2-methylenenaphthyl)ethylidene)dihydro-4-hydroxyfuran-2(3H)-one.

In one aspect of this embodiment the compositions further comprise a compound selected from the group consisting of (4S,5S)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one; (4R,5R)-3,4-dihydroxy-4-[(1R)-hydroxy-4-methylpent-3-en-1-yl]-2-(3-methylbutanoyl)-5-(3-methylbut-2-en-1-yl)cyclopent-2-en-1 one; (4R,5R)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one; (4R,5R)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one; (4R,5R)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one; (4R,5R)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one; (4R,5R)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one; (4R,5S)-3,4-dihydroxy-4-[(1R)-hydroxy-4-methylpent-3-en-1-yl]-2-(3-methylbutanoyl)-5-(3- methylbut-2-en-1-yl)cyclopent-2-en-1-one; (4R,5S)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one; (4R,5S)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one; (4R,5S)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one; (4R,5S)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one; (4R,5S)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one; (4S,5R)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one; (4S,5R)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one; (4S,5R)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one; (4S,5R)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one; (4S,5R)-3,4-dihydroxy-4-[(1S)-hydroxy-4-methylpent-3-en-1-yl]-2-(2-methylpropanoyl)-5-(3-methylbut-2-en-1-yl)cyclopent-2-en-1-one; (4S,5R)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one; (4S,5S)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one; (4S,5S)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one; (4S,5S)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one; (4S,5S)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one; and (4S,5S)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one.

In a further aspect of the embodiment, the compositions further comprise a compound selected from the group consisting of 4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; and (4R,5S)-3,4-dihydroxy-2-(3-methylbutanoyl)-5-(3-methylbutyl)-4-(4-methylpentanoyl)cyclopent-2-en-1-one.

Compositions further comprising a compound selected from the group consisting of (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; and (4S,5S)-3,4-dihydroxy-4-[(1S)-1-hydroxy-4-methylpentyl]-2-(3-methylbutanoyl)-5-(3-methylbutyl)cyclopent-2-en-1-one are described in yet another aspect of this embodiment.

In some aspects of this embodiment the compositions further comprise a pharmaceutically acceptable excipient selected from the group consisting of coatings, isotonic and absorption delaying agents, binders, adhesives, lubricants, disintegrants, coloring agents, flavoring agents, sweetening agents, absorbants, detergents, and emulsifying agents. In other aspects, the compositions further comprise one or more members selected from the group consisting of antioxidants, vitamins, minerals, proteins, fats, and carbohydrates.

As used herein, "promoting heavy metal detoxification" refers to inducing detoxification enzyme production, augmenting the enzymatic activity of existing detoxification enzymes, or inhibiting the inhibitors of the detoxification enzymes. Representative, non-limiting examples of detoxification enzymes include alcohol sulphotransferase, amine N-methyltransferase, amine O-sulphotransferase, arylamine N-acetyltransferase (NAT2), catechol O-methyltransferase, cysteine conjugate β-lyase, cysteine N-acetyltransferase, glycine acyltransferase, glutamate acyltransferase, glutathione S-transferases (GST), heme oxygenase-1, histamine N-methyltransferase, microsomal epoxide hydrolase (mEH), metallothioneins, NAD(P)H: quinone oxidoreductase (NQO1), phenol O-methyltransferase, phenol sulphotransferase, rhodanese, thiol S-methyltransferase, thioltransferase, and UDP-glucuronosyl transferase (UDP-GT).

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, "compounds" may be identified either by their chemical structure, chemical name, or common name. When the chemical structure and chemical or common name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated or identified compounds. The compounds described also encompass isotopically labeled compounds where one or more atoms have an atomic mass different from the atomic mass conventionally found in nature. Examples of isotopes that may be incorporated into the compounds of the invention include, but are not limited to, $^2H$, $^3H$, $^{13}C$, $^{14}C$, $^{15}N$, $^{18}O$, $^{17}O$, etc. Compounds may exist in unsolvated forms as well as solvated forms, including hydrated forms and as N-oxides. In general, compounds may be hydrated, solvated or N-oxides. Certain compounds may exist in multiple crystalline or amorphous forms. Also contemplated within the scope of the invention are congeners, analogs, hydrolysis products, metabolites and precursor or prodrugs of the compound. In general, unless otherwise indicated, all physical forms are equivalent for the uses contemplated herein and are intended to be within the scope of the present invention.

Compounds according to the invention may be present as salts. In particular, pharmaceutically acceptable salts of the compounds are contemplated. A "pharmaceutically acceptable salt" of the invention is a combination of a compound of the invention and either an acid or a base that forms a salt (such as, for example, the magnesium salt, denoted herein as "Mg" or "Mag") with the compound and is tolerated by a subject under therapeutic conditions. In general, a pharmaceutically acceptable salt of a compound of the invention will have a therapeutic index (the ratio of the lowest toxic dose to the lowest therapeutically effective dose) of 1 or greater. The person skilled in the art will recognize that the lowest therapeutically effective dose will vary from subject to subject and from indication to indication, and will thus adjust accordingly.

The compositions according to the invention are optionally formulated in a pharmaceutically acceptable vehicle with any of the well known pharmaceutically acceptable carriers, including diluents and excipients (see Remington's Pharmaceutical Sciences, 18th Ed., Gennaro, Mack Publishing Co., Easton, Pa. 1990 and Remington: The Science and Practice of Pharmacy, Lippincott, Williams & Wilkins, 1995). While the type of pharmaceutically acceptable carrier/vehicle employed in generating the compositions of the invention will vary depending upon the mode of administration of the composition to a mammal, generally pharmaceutically acceptable carriers are physiologically inert and non-toxic. Formulations of compositions according to the invention may contain more than one type of compound of the invention), as well any other pharmacologically active ingredient useful for the treatment of the symptom/condition being treated. The term "pharmaceutically acceptable" is used in the sense of being compatible with the other ingredients of the compositions and not deleterious to the recipient thereof.

As used herein "hop" or "hops" refers to plant cones of the genus *Humulus* which contain a bitter aromatic oil which is used in the brewing industry to prevent bacterial action and add the characteristic bitter taste to beer. More preferably, the hops used are derived from *Humulus lupulus*.

The term "therapeutically effective amount" is used to denote treatments at amounts of the compositions effective to achieve the therapeutic result sought. Furthermore, one of skill will appreciate that the therapeutically effective amount may be lowered or increased by fine tuning and/or by administering more than one composition of the invention, or by administering a composition of the invention with another composition or compound. See, for example, Meiner, C. L., "Clinical Trials: Design, Conduct, and Analysis," Monographs in Epidemiology and Biostatistics, Vol. 8 Oxford University Press, USA (1986). The invention therefore provides a method to tailor the administration/treatment to the particular exigencies specific to a given mammal. As illustrated in the following examples, therapeutically effective amounts may be easily determined for example empirically by starting at relatively low amounts and by step-wise increments with concurrent evaluation of beneficial effect.

As used herein, the term "spent hops" refers to the solid and hydrophilic residue resulting from (1) exposing a hops plant product to a solvent, (2) separating the solvent from the hops plant products, and (3) eliminating the solvent. Representative solvents, without limitation, can include CO2, water, organic solvents (e.g., alcohols) or mixtures thereof.

1,7-Bis(4-hydroxy-3-methoxyphenyl)hepta-1,6-diene-3,5-dione is presented graphically in FIG. 1. As used herein, "1,7-Bis(4-hydroxy-3-methoxyphenyl)hepta-1,6-diene-3,5-dione" refers to curcumin, a yellow pigmented fraction isolated from the rhizomes of *Curcuma longa*. The curcuminoids are considered the important active ingredients and are believed to be responsible for the biological activity of *Curcuma longa*. Though their major activity is anti-inflammatory, curcuminoids have been reported to possess antioxidant, antiallergic, wound healing, antispasmodic, antibacterial, antifungal and antitumor activity as well.

Figure 2:
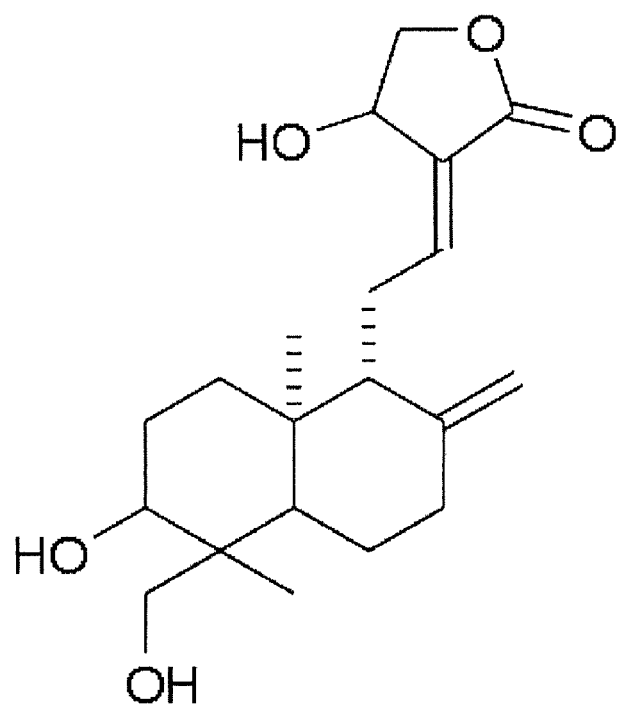
FIG. 2 is a graphic representation of the chemical structure of 3-(2-(Decahydro-6-hydroxy-5-(hydroxymethyl)-5,8a-dimethyl-2-methylenenaphthyl)ethylidene)dihydro-4-hydroxyfuran-2(3H)-one.

3-(2-(Decahydro-6-hydroxy-5-(hydroxymethyl)-5,8a-dimethyl-2-methylenenaphthyl)ethylidene)dihydro-4-hydroxyfuran-2(3H)-one is presented graphically in FIG. 2. As used herein, "3-(2-(Decahydro-6-hydroxy-5-(hydroxymethyl)-5,8a-dimethyl-2-methylenenaphthyl)ethylidene)dihydro-4-hydroxyfuran-2(3H)-one" refers to andrographolide/ *andrographis*, a diterpene lactone. Diterpene lactone species, such as andrographolide are commonly found in plants and are used for their anti-inflammatory properties. Their mechanism of action is believed to be due (i) to the inhibition of histamine release from mast cells or (ii) to the inhibition of lipoxygenase and cyclooxygenase activity thereby reducing the synthesis of inflammatory factors produced during the arachidonic acid cascade.

As used herein, the term "reduced isoalpha acid" refers to alpha acids isolated from hops plant product and subsequently have been isomerized and reduced, including cis and trans forms. Examples of reduced isoalpha acids (RIAA) include without limitation dihydro-isoalpha acids, more specifically Rho dihydro-isoalpha acids (Table 1), tetra-hydroisoalpha acid (Table 2), and hexa-hydroisoalpha acids (Table 3), and their derivatives. "Rho" refers to those reduced isoalpha acids wherein the reduction is a reduction of the carbonyl group in the 4-methyl-3-pentenoyl side chain.

TABLE 1

| Rho dihydro-isoalpha acids | | |
|---|---|---|
| Chemical Name | Synonym | Structure |
| (4S,5S)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one | rho (6S) cis n iso-alpha acid | |
| (4S,5S)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one | rho (6R) cis n iso-alpha acid | |
| (4R,5S)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one | rho (6R) trans n iso-alpha acid | |

TABLE 1-continued

Rho dihydro-isoalpha acids

| Chemical Name | Synonym | Structure |
| --- | --- | --- |
| (4R,5S)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one | rho (6S) trans n iso-alpha acid | 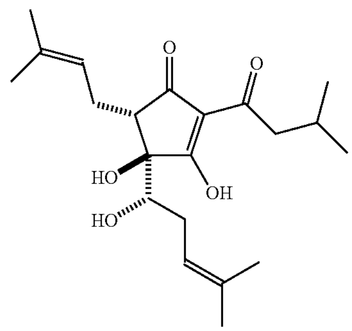 |
| (4R,5R)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one | rho (6R) cis rho n iso-alpha acid | 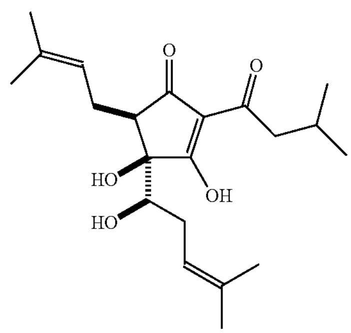 |
| (4R,5R)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one | rho (6S) cis n iso-alpha acid | 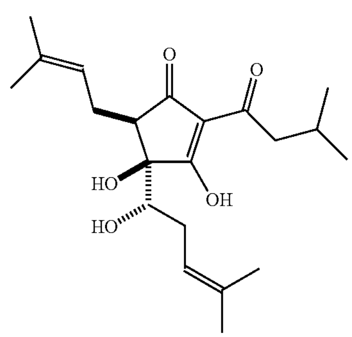 |
| (4S,5R)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one | (6S) trans rho n iso-alpha acid | 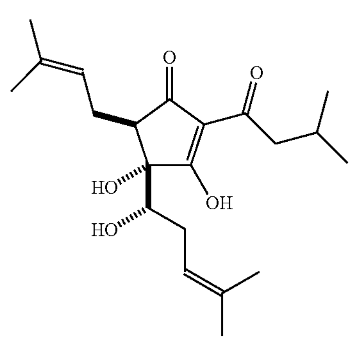 |

TABLE 1-continued

Rho dihydro-isoalpha acids

| Chemical Name | Synonym | Structure |
| --- | --- | --- |
| (4S,5R)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one | rho (6R) trans n iso-alpha acid | 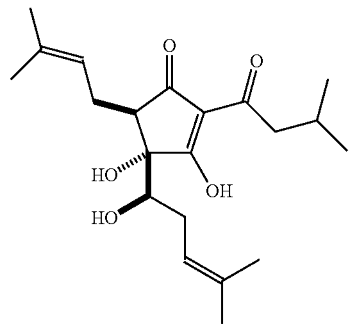 |
| (4S,5S)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one | rho (6S) cis co iso-alpha acid | 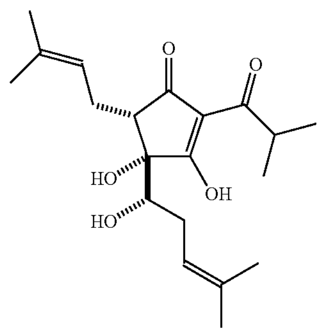 |
| (4S,5S)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one | rho (6R) cis co iso-alpha acid | 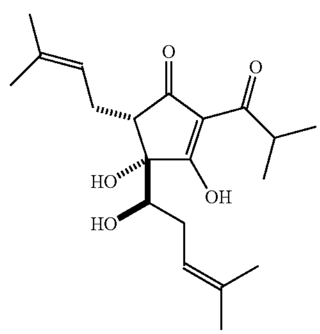 |
| (4R,5S)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one | rho (6R) trans co iso-alpha acid | 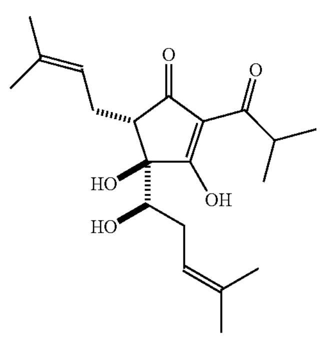 |

TABLE 1-continued

Rho dihydro-isoalpha acids

| Chemical Name | Synonym | Structure |
| --- | --- | --- |
| (4R,5S)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one | rho (6S) trans co iso-alpha acid | 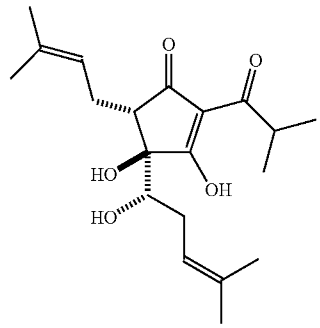 |
| (4R,5R)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one | rho (6R) cis co iso-alpha acid | 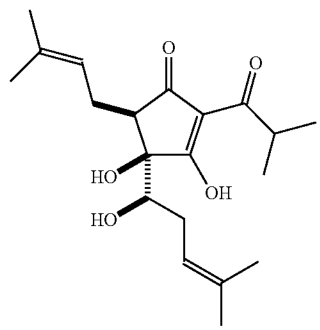 |
| (4R,5R)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one | rho (6S) cis co iso-alpha acid | 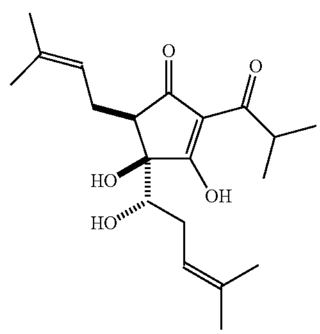 |
| (4S,5R)-3,4-dihydroxy-4-[(1S)-hydroxy-4-methylpent-3-en-1-yl]-2-(2-methylpropanoyl)-5-(3-methylbut-2-en-1-yl)cyclopent-2-en-1-one | rho (6S) trans co iso-alpha acid | 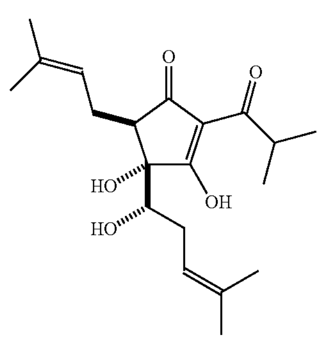 |

TABLE 1-continued

Rho dihydro-isoalpha acids

| Chemical Name | Synonym | Structure |
|---|---|---|
| (4S,5R)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one | rho (6R) trans co iso-alpha acid | 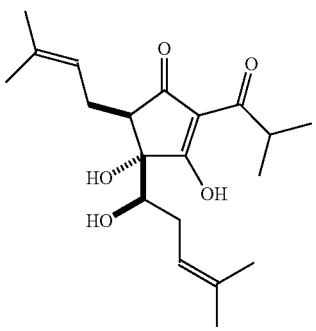 |
| (4S,5S)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one | rho (6S) cis ad iso-alpha acid | 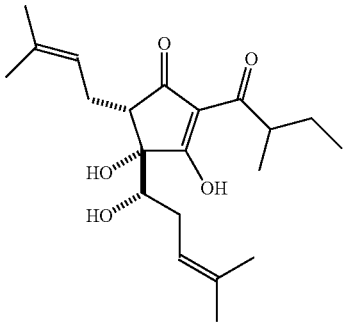 |
| (4S,5S)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one | rho (6R) cis ad iso-alpha acid | 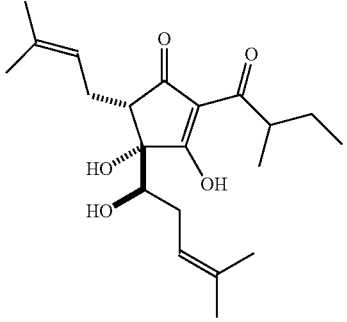 |
| (4R,5S)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one | rho (6R) trans ad iso-alpha acid | 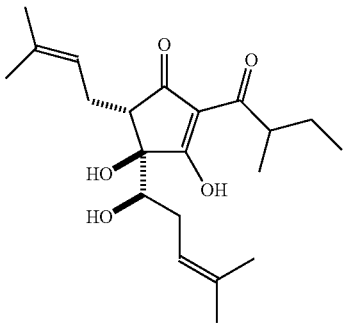 |

TABLE 1-continued

Rho dihydro-isoalpha acids

| Chemical Name | Synonym | Structure |
|---|---|---|
| (4R,5S)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one | rho (6S) trans ad iso-alpha acid | 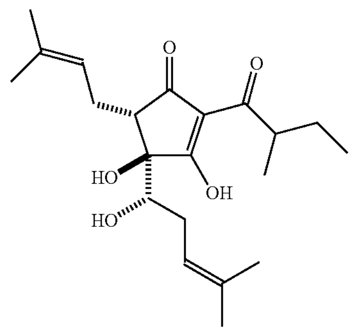 |
| (4R,5R)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one | rho (6R) cis ad iso-alpha acid | 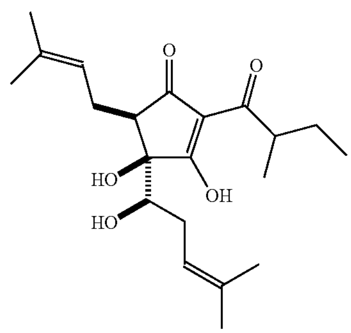 |
| (4R,5R)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one | rho (6S) cis ad iso-alpha acid | 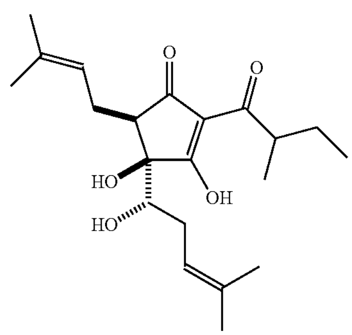 |
| (4S,5R)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one | rho (6S) trans iso-alpha | 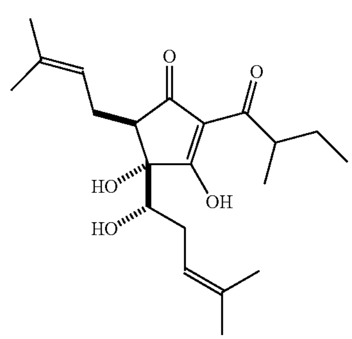 |

TABLE 1-continued

| Rho dihydro-isoalpha acids | | |
|---|---|---|
| Chemical Name | Synonym | Structure |
| (4S,5R)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one | rho (6R) trans ad iso-alpha acid | 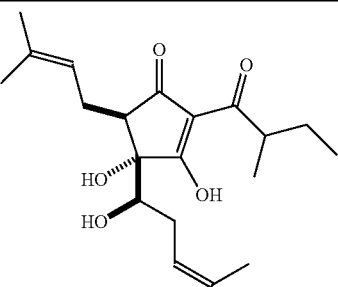 |

TABLE 2

| Tetrahydro-isoalpha acids | | |
|---|---|---|
| Chemical Name | Synonym | Structure |
| (4R,5S)-3,4-dihydroxy-2-(3-methylbutanoyl)-5-(3-methylbutyl)-4-(4-methylpentanoyl)cyclopent-2-en-1-one | tetrahydro cis n iso-alpha acid | |
| (4S,5S)-3,4-dihydroxy-2-(3-methylbutanoyl)-5-(3-methylbutyl)-4-(4-methylpentanoyl)cyclopent-2-en-1-one | tetrahydro trans n iso-alpha acid | |
| (4S,5R)-3,4-dihydroxy-2-(3-methylbutanoyl)-5-(3-methylbutyl)-4-(4-methylpentanoyl)cyclopent-2-en-1-one | tetrahydro cis n iso-alpha acid | |

TABLE 2-continued

| Tetrahydro-isoalpha acids | | |
|---|---|---|
| Chemical Name | Synonym | Structure |
| (4R,5R)-3,4-dihydroxy-2-(3-methylbutanoyl)-5-(3-methylbutyl)-4-(4-methylpentanoyl)cyclopent-2-en-1-one | tetrahydro trans n iso-alpha acid | |
| (4R,5S)-3,4-dihydroxy-5-(3-methylbutyl)-4-(4-methylpentanoyl)-2-(3-methylpropanoyl)cyclopent-2-en-1-one | tetrahydro cis co iso-alpha acid | |
| (4S,5S)-3,4-dihydroxy-5-(3-methylbutyl)-4-(4-methylpentanoyl)-2-(3-methylpropanoyl)cyclopent-2-en-1-one | tetrahydro trans co iso-alpha acid | |
| (4S,5R)-3,4-dihydroxy-5-(3-methylbutyl)-4-(4-methylpentanoyl)-2-(3-methylpropanoyl)cyclopent-2-en-1-one | tetrahydro cis co iso-alpha acid | |

TABLE 2-continued

Tetrahydro-isoalpha acids

| Chemical Name | Synonym | Structure |
|---|---|---|
| (4R,5R)-3,4-dihydroxy-5-(3-methylbutyl)-4-(4-methylpentanoyl)-2-(3-methylpropanoyl)cyclopent-2-en-1-one | tetrahydro trans co iso-alpha acid | 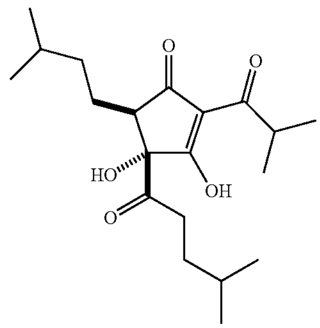 |
| (4R,5S)-3,4-dihydroxy-2-(2-methylbutanoyl)-5-(3-methylbutyl)-4-(4-methylpentanoyl)cyclopent-2-en-1-one | tetrahydro cis ad iso-alpha acid | 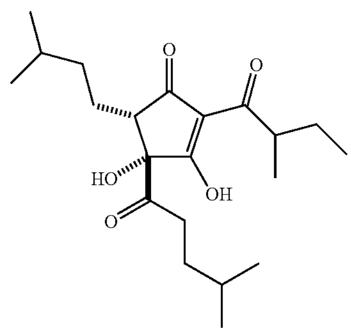 |
| (4S,5S)-3,4-dihydroxy-2-(2-methylbutanoyl)-5-(3-methylbutyl)-4-(4-methylpentanoyl)cyclopent-2-en-1-one | tetrahydro trans ad iso-alpha acid | 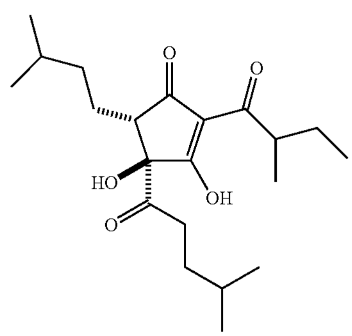 |
| (4S,5R)-3,4-dihydroxy-2-(2-methylbutanoyl)-5-(3-methylbutyl)-4-(4-methylpentanoyl)cyclopent-2-en-1-one | tetrahydro cis ad iso-alpha acid | 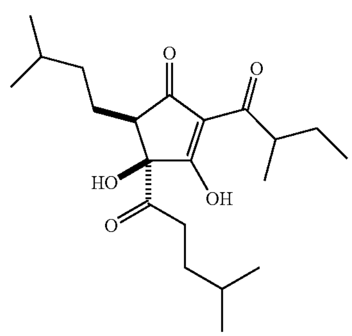 |

TABLE 2-continued

Tetrahydro-isoalpha acids

| Chemical Name | Synonym | Structure |
|---|---|---|
| (4R,5R)-3,4-dihydroxy-2-(2-methylbutanoyl)-5-(3-methylbutyl)-4-(4-methylpentanoyl)cyclopent-2-en-1-one | tetrahydro trans ad iso-alpha acid | |

TABLE 3

Hexahydro-isoalpha acids

| Chemical Name | Synonym | Structure |
|---|---|---|
| (4S,5S)-3,4-dihydroxy-4-[(1S)-1-hydroxy-4-methylpentyl]-2-(3-methylbutanoyl)-5-(3-methylbutyl)cyclopent-2-en-1-one | hexahydro (6S) cis n iso-alpha acid | 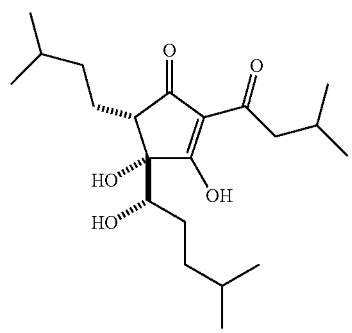 |
| (4S,5S)-3,4-dihydroxy-4-[(1R)-1-hydroxy-4-methylpentyl]-2-(3-methylbutanoyl)-5-(3-methylbutyl)cyclopent-2-en-1-one | hexahydro (6R) cis n iso-alpha acid | 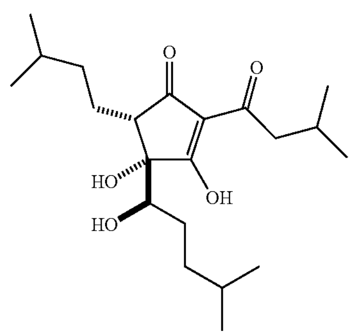 |
| (4R,5S)-3,4-dihydroxy-4-[(1R)-1-hydroxy-4-methylpentyl]-2-(3-methylbutanoyl)-5-(3-methylbutyl)cyclopent-2-en-1-one | hexahydro (6R) trans n iso-alpha acid | 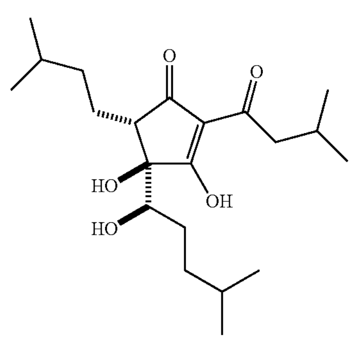 |

TABLE 3-continued

Hexahydro-isoalpha acids

| Chemical Name | Synonym | Structure |
| --- | --- | --- |
| (4R,5S)-3,4-dihydroxy-4-[(1S)-1-hydroxy-4-methylpentyl]-2-(3-methylbutanoyl)-5-(3-methylbutyl)cyclopent-2-en-1-one | hexahydro (6S) trans n iso-alpha acid | 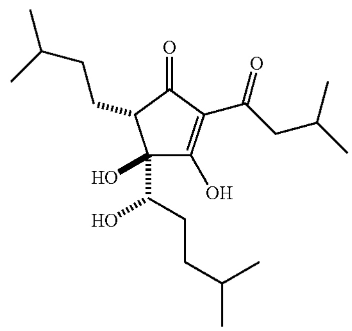 |
| (4R,5R)-3,4-dihydroxy-4-[(1R)-1-hydroxy-4-methylpentyl]-2-(3-methylbutanoyl)-5-(3-methylbutyl)cyclopent-2-en-1-one | hexahydro (6R) cis n iso-alpha acid | 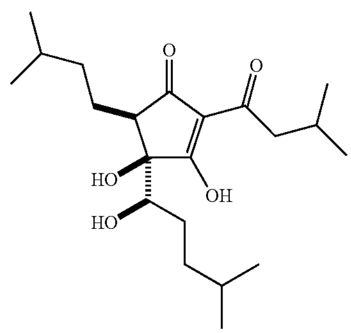 |
| (4R,5R)-3,4-dihydroxy-4-[(1S)-1-hydroxy-4-methylpentyl]-2-(3-methylbutanoyl)-5-(3-methylbutyl)cyclopent-2-en-1-one | hexahydro (6S) cis n iso-alpha acid | 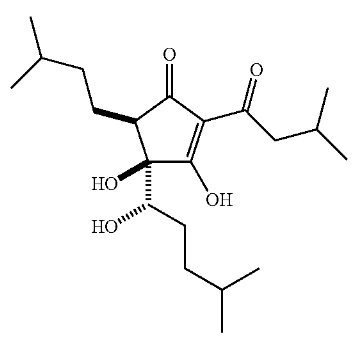 |
| (4S,5R)-3,4-dihydroxy-4-[(1S)-1-hydroxy-4-methylpentyl]-2-(3-methylbutanoyl)-5-(3-methylbutyl)cyclopent-2-en-1-one | hexahydro (6S) trans n iso-alpha acid | 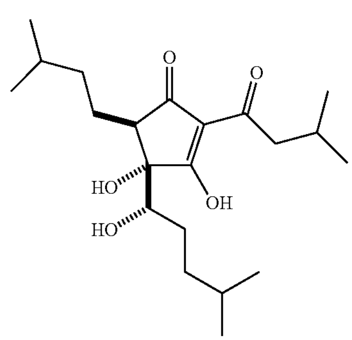 |

TABLE 3-continued

Hexahydro-isoalpha acids

| Chemical Name | Synonym | Structure |
| --- | --- | --- |
| (4S,5R)-3,4-dihydroxy-4-[(1R)-1-hydroxy-4-methylpentyl]-2-(3-methylbutanoyl)-5-(3-methylbutyl)cyclopent-2-en-1-one | hexahydro (6R) trans n iso-alpha acid | 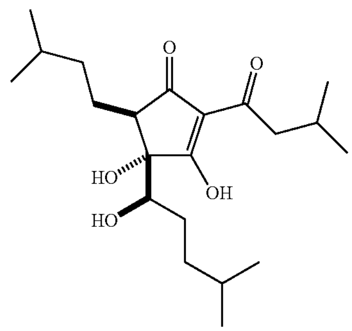 |
| (4S,5S)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one | hexahydro (6S) cis co iso-alpha acid | 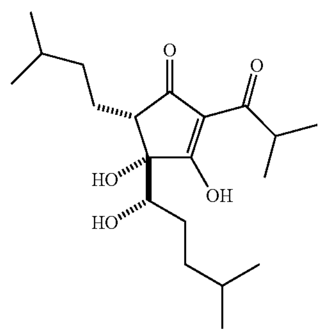 |
| (4S,5S)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one | hexahydro (6R) cis co iso-alpha acid | 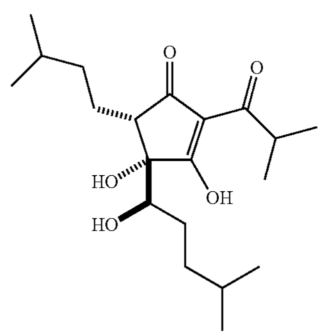 |
| (4R,5S)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one | hexahydro (6R) trans co iso-alpha acid | 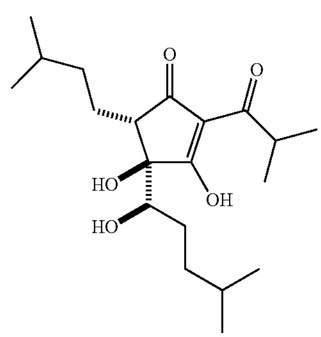 |

TABLE 3-continued

Hexahydro-isoalpha acids

| Chemical Name | Synonym | Structure |
| --- | --- | --- |
| (4R,5S)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one | hexahydro (6S) trans co iso-alpha acid | 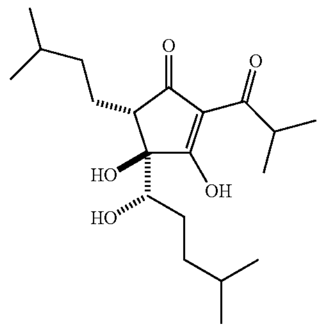 |
| (4R,5R)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one | hexahydro (6R) cis co iso-alpha acid | 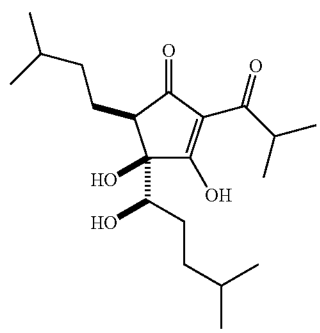 |
| (4R,5R)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one | hexahydro (6S) cis co iso-alpha acid | 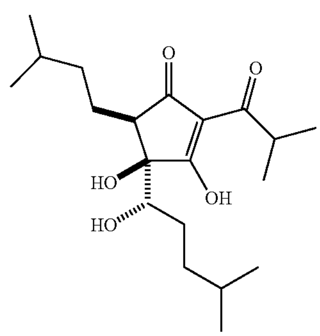 |
| (4S,5R)-3,4-dihydroxy-4-[(1S)-hydroxy-4-methylpent-3-en-1-yl]-2-(2-methylpropanoyl)-5-(3-methylbut-2-en-1-yl)cyclopent-2-en-1-one | hexahydro (6S) trans co iso-alpha acid | 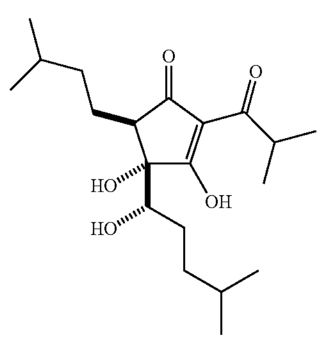 |

TABLE 3-continued

Hexahydro-isoalpha acids

| Chemical Name | Synonym | Structure |
| --- | --- | --- |
| (4S,5R)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one | hexahydro (6R) trans co iso-alpha acid | 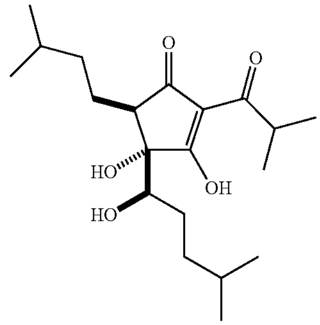 |
| (4S,5S)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one | hexahydro (6S) cis ad iso-alpha acid | 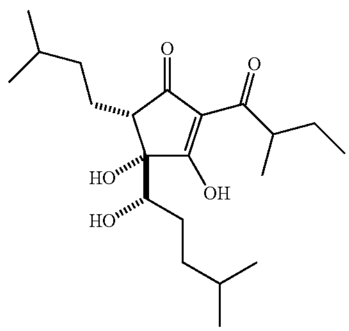 |
| (4S,5S)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one | hexahydro (6R) cis ad iso-alpha acid | 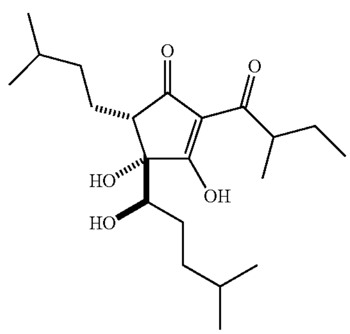 |
| (4R,5S)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one | hexahydro (6R) trans ad iso-alpha acid | 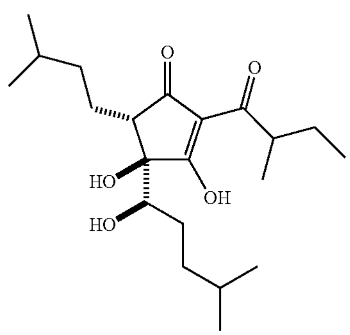 |

TABLE 3-continued

| Hexahydro-isoalpha acids | | |
|---|---|---|
| Chemical Name | Synonym | Structure |
| (4R,5S)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one | hexahydro (6S) trans ad iso-alpha acid | |
| (4R,5R)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one | hexahydro (6R) cis ad iso-alpha acid | |
| (4R,5R)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one | hexahydro (6S) cis ad iso-alpha acid | |
| (4S,5R)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one | hexahydro (6S) trans ad iso-alpha acid | |

TABLE 3-continued

Hexahydro-isoalpha acids

| Chemical Name | Synonym | Structure |
| --- | --- | --- |
| (4S,5R)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one | hexahydro (6R) trans ad iso-alpha acid | 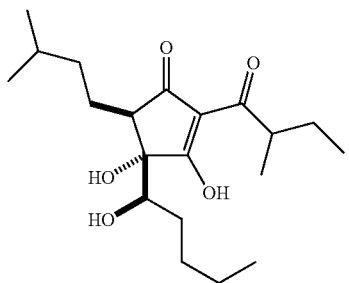 |

As used herein, the terms "derivatives" or a matter "derived from" refer to a chemical substance related structurally to another substance and theoretically obtainable from it, i.e. a substance that can be made from another substance. Derivatives can include compounds obtained via a chemical reaction or de novo chemical syntheses. See Verzele, M. and De Keukeleire, D., *Developments in Food Science* 27: *Chemistry and Analysis of Hop and Beer Bitter Acids*, Elsevier Science Pub. Co., 1991, New York, USA, herein incorporated by reference in its entirety, for a detailed discussion of hops chemistry.

A second embodiment of the invention describes methods for promoting heavy metal detoxification in a mammal, where the methods utilize compositions which comprise a therapeutically effective amount of at least two members selected from the group consisting of spent hops; 1,7-Bis(4-hydroxy-3-methoxyphenyl)hepta-1,6-diene-3,5-dione; zinc; and 3-(2-(Decahydro-6-hydroxy-5-(hydroxymethyl)-5,8a-dimethyl-2-methylenenaphthyl)ethylidene)dihydro-4-hydroxyfuran-2(3H)-one.

In one aspect of this embodiment the compositions of the method further comprise a compound selected from the group consisting of (4S,5S)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one; (4R,5R)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one; (4R,5R)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one; (4R,5R)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one; (4R,5R)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one; (4R,5R)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one; (4R,5R)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one; (4R,5S)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one; (4R,5S)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one; (4R,5S)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one; (4R,5S)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one; (4R,5S)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one; (4S,5R)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one; (4S,5R)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one; (4S,5R)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one; (4S,5R)-3,4-dihydroxy-4-[(1S)-hydroxy-4-methylpent-3-en-1-yl]-2-(2-methylpropanoyl)-5-(3-methylbut-2-en-1-yl)cyclopent-2-en-1-one; (4S,5R)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one; (4S,5S)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one; (4S,5S)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one; (4S,5S)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one; (4S,5S)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one; and (4S,5S)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one.

In a further aspect of the embodiment, the compositions of the method further comprise a compound selected from the group consisting of 4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3, 4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; and (4R,5S)-3,4-dihydroxy-2-(3-methylbutanoyl)-5-(3-methylbutyl)-4-(4-methylpentanoyl)cyclopent-2-en-1-one.

Compositions of the method further comprising a compound selected from the group consisting of (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4'-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; and (4S,5S)-3,4-dihydroxy-4-[(1S)-1-hydroxy-4-methylpentyl]-2-(3-methylbutanoyl)-5-(3-methylbutyl)cyclopent-2-en-1-one are described in yet another aspect of this embodiment.

In some aspects of this embodiment the compositions used further comprise a pharmaceutically acceptable excipient selected from the group consisting of coatings, isotonic and absorption delaying agents, binders, adhesives, lubricants, disintegrants, coloring agents, flavoring agents, sweetening agents, absorbants, detergents, and emulsifying agents. In other aspects the compositions of the methods further comprise one or more members selected from the group consisting of antioxidants, vitamins, minerals, proteins, fats, and carbohydrates.

The methods of the present invention are intended for use with any mammal that may experience the benefits of the methods of the invention. Foremost among such mammals are humans, although the invention is not intended to be so limited, and is applicable to veterinary uses. Thus, in accordance with the invention, "mammals" or "mammals in need" include humans as well as non-human mammals, particularly domesticated animals including, without limitation, cats, dogs, and horses.

A composition comprising: from about 0.10 to about 10.00 grams of spent hops; from about 5 to about 1200 mg of 1,7-Bis(4-hydroxy-3-methoxyphenyl)hepta-1,6-diene-3,5-dione; from about 0.10 to about 24 mg of zinc; and from about 5 to about 1200 mg of 3-(2-(Decahydro-6-hydroxy-5-(hydroxymethyl)-5,8a-dimethyl-2-methylenenaphthyl)ethylidene)dihydro-4-hydroxyfuran-2(3H)-one is described in a third embodiment of the invention while a further embodiment of the invention describes methods for promoting heavy metal detoxification in a mammal, where the methods utilize compositions comprising from about 0.10 to about 10.00 grams of spent hops; from about 5 to about 1200 mg of 1,7-Bis(4-hydroxy-3-methoxyphenyl)hepta-1,6-diene-3,5-dione; from about 0.10 to about 24 mg of zinc; and from about 5 to about 1200 mg of 3-(2-(Decahydro-6-hydroxy-5-(hydroxymethyl)-5,8a-dimethyl-2-methylenenaphthyl)ethylidene)dihydro-4-hydroxyfuran-2(3H)-one.

A further embodiment of the invention describes methods for promoting heavy metal detoxification in a mammal utilizing a composition comprising a therapeutically effective amount of spent hops.

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

EXAMPLES

Example 1

Effects of Test Compounds on Detoxification Enzyme Activity

Test Materials—All test compounds were supplied by Metagenics (San Clemente, Calif., USA). Test compounds were prepared in dimethyl sufoxide (DMSO) and stored at −20° C. Sulforaphane, glutathione and 1-Chloro 2,4-dinitro benzene (CDNB) were purchased from Sigma Chemicals (St. Louis, Mo.). All other general chemicals were analytical grade.

Cell culture and treatment—The rat liver cell line RL-34 was purchased from the Japan Health Science Foundation (Tokyo, Japan). Cells were maintained in log phase in DMEM media supplemented with 5% heat inactivated FBS, 100 IU penicillin, and 100 µg/ml streptomycin. The human liver cell line HepG2 was purchased from ATCC (Manassas, Va.). Cells were maintained in log phase in MEM media supplemented with 10% heat inactivated FBS, 100 IU penicillin, and 100 µg/ml streptomycin.

Enzymatic activity in RL-34 cells—Cells were subcultured in 6-well plates at a density of $3 \times 10^5$ cells per well. The following day test compounds in DMSO were added at a final 0.1% DMSO concentration. The cells were incubated with test compound for 2 days in a humidified incubator at 37° C. after which the cells were lysed and assayed for enzyme activity. Following treatment with test compounds, cells were washed twice with 0.5 ml PBS and all residual liquid was removed. To lyse the cells, 150 µL Buffer D (0.8% digitonin in 2 mM EDTA) was added to each well and incubated for 15 minutes at room temperature. The cell lysate was centrifuged for 10 minutes at 10,000 rpm. The supernatant containing the cell lysate was transferred into a 96-well plate. Protein determination was performed using the Bicinchoninic Acid Kit (Sigma, St. Louis, Mo.). Equal protein concentrations were used in all enzyme activity assays.

GST activity assay—Cell lysate (20 µL) containing the GST enzyme was added to each well of a UV flat bottom 96 well microtiter plate. Reaction buffer was added (300 µL) to each well to achieve a final concentration of 8 mM glutathione and 3.2 mM CDNB in 100 mM $KPO_4$. The enzymatic conversion of CDNB was measured at 340 nm over three minutes to determine a rate of GST activity (Apati, P., et al., J Pharm Pharmacol, 58(2): 251-6, 2006, and Habig, W. H., M. J. Pabst, and W. B. Jakoby, J Biol Chem., 249: 7130-9, 1974).

NADPH quinone oxido reductase assay (NQO1)—To assay NQO1 activity, 20 µL of cell lysate containing the NQO1 enzyme was added to each well of a flat bottom 96 well microtiter plate. Reaction buffer was added (200 µL) to each well to achieve a final concentration of 25 mM Tris-HCl, pH 7.4, 5 µM FAD, 1 mM G6P, 30 µM NADP, 2 U/ml G6PDH, 0.06% BSA, 725 µM MTT and 50 µM menadione. The reduction of MTT at 610 nm was measured after three minutes to determine the induction of NQO1 activity (Feng, R., et al., J Biol Chem, 280(30): 27888-95, 2005. and Prochaska, H. J. and A. B. Santamaria, Anal Biochem., 169: 328-36, 1988). The induction of NQO1 activity was determined as the ratio of treated over vehicle control.

Co-transfection of Reporter and Expression Plasmids—Construction of the heme oxygenase reporter was described previously (Gong, P., et al., Arch Biochem Biophys, 405(2): 265-74, 2002). The Lipofectamine 2000 transfection reagent from Invitrogen was used to perform the transfections by procedures as described in the manufacturer's protocol. HepG2 cells were subcultured in 96-well white plates at a density of $5 \times 10^4$ cells per well in MEM medium without serum and antibiotics. The following day dilute HO-1 reporter construct with pRL-TK (0.2 µg total DNA in a ratio of 2:1) in 25 µL of opti-MEM and mix gently. Dilute 0.5 µL of Lipofectamine 2000 in 25 µL, of opti-MEM and incubate for 5 minutes at room temperature. Then combine the diluted DNA with diluted Lipofectamine 2000, mix gently and incubate for 20 min at room temperature. The cells were incubated with 50 µl of above complex for 6 hours in a humidified incubator at 37° C. After 6 hours of incubation, 100 µL, MEM medium without serum and antibiotics were added and incubated for 18 hours. The medium was discarded and test compounds in DMSO were added at a final 0.1% DMSO concentration for 24 hours. The plasmid pRL-TK encoding *Renilla* luciferase was used as the internal control of each transfection.

Luciferase activity—Two days after the transfection, cells were washed with phosphate-buffered saline and lysed in passive lysis buffer from the Dual Luciferase reporter assay system per the manufacturer's protocol (Promega). First, the cell lysate was assayed for the firefly luciferase activity using 100 µl of the substrate LARII. Then 100 µl of the STOP & GLO reagent was added to quench the firefly luciferase activity and activate the *Renilla* luciferase, which was also measured. The assays were carried out in a PerkinElmer luminometer, and the relative luciferase activity was calculated as follows: 100,000/activity of *Renilla* luciferase (in units) 3 activity of firefly luciferase (in units). Each set of transfections was repeated three times.

Quantitative PCR—HepG2 cells were subcultured in 6-well plates at a density of $3 \times 10^5$ cells per well. The following day test compounds in DMSO were added at a final 0.1% DMSO concentration. The cells were incubated with test compound for 8 hours in a humidified incubator at 37° C. The mRNA was then purified for gene expression analysis using TRI reagent (Sigma Chemicals) according to the manufacture's instructions. Following mRNA purification, the cDNA template was generated for use in the QPCR analysis. This was performed with the Omniscript RT kit (Qiagen, Valencia, Calif.) at 37° C. for 60 min in a Techgene thermocycler (Techne, Burlington, N.J.) to yield a 20 µL reaction with 2 µg starting mRNA. The blinded samples were sent to Dr. John Tine at the Center for Functional Genomics, University at Albany (Renesselaer, N.Y.). Quantitative PCR was performed utilizing Taqman® chemistry and ΔΔCt quantification. Assays were performed in triplicate with 20 ng total RNA per well and GADPH as the internal control. The remaining five genes analyzed were GSTA1, NQO1, HMOX1, and two groupings of metallothioneins, hMT1&2 and hMT1&2alt. The protocol for metallothionein gene expression was taken from the work by Aydemir et al (Proc Natl Acad Sci USA, 103(6): 1699-704, 2006), where a combination of two forward primers, two reverse primers, and two Taqman® probes gave matches for MT1H, -1H-like, -1G, -1L, -1E, -1A, and MT2.

Western blot detection—The HepG2 cell line was cultured as above and test compounds were added for four hours, after which the cells were lysed and the nuclear fraction was isolated (Dignam, J. D., R. M. Lebovitz, and R. G. Roeder, Nucleic Acids Res, 11(5): 1475-89, 1983). Total protein concentration was determined using the Bicinchoninic Acid Kit (Sigma). Total cell lysates (60 µg total protein) were electrophoresed and detection of Nrf-2 was performed using primary antibody incubation overnight at 4° C. (Santa Cruz Biotechnology, Inc, Santa Cruz, Calif.). Secondary antibody linked to horseradish peroxidase was incubated for one h (GE Healthcare, Piscataway, N.J.), after which proteins were visualized using the enhanced chemiluminescence (ECL) system. Densitometry was performed using Kodak Molecular Imaging Software v.4.0 (Eastman Kodak Company, Rochester, N.Y.) measuring the net intensity of the band.

Statistical analysis—The induction of GST and NADPH quinone reductase assay activity were determined as the ratio of treated with test compounds over vehicle (DMSO) control.

GST and NQO1 activity was normalized for equal protein. A minimum of two wells were used for each condition. The induction of heme oxygenase promoter activity was determined as the ratio of treated with test compounds over vehicle control. Luciferase activity was normalized with *Renilla* luciferase activity as a control. A minimum of 4 wells were used for each condition. The data represents the average of three independent experiments (SEM).

Results

Enzymatic Activity—Sulforaphane is a known activator of Nrf-2 and was used as a control in the enzymatic activity assays. According to the convention of the scientific literature, 20% induction of activity by test compounds over DMSO control is considered active. GST activity (Table 4) was induced≧20% by Sulforaphane (3 μg/ml), *Andrographis* (25 μg/ml), Xanthohumol (1 μg/ml), Prune (20 μg/ml), *Withania* (20 μg/ml), Osteosine (20 μg/ml), MCHA (20 μg/ml), and Arthred Porcine (20 μg/ml) in RL-34 cell line. NQO1 enzymatic activity (Table 5) was induced≧20% by (1,7-Bis (4-hydroxy-3-methoxyphenyl)hepta-1,6-diene-3,5-dione) (curcumin) (5 μg/ml), (3-(2-(Decahydro-6-hydroxy-5-(hydroxymethyl)-5,8a-dimethyl-2-methylenenaphthyl)ethylidene)dihydro-4-hydroxyfuran-2(3H)-one) (*andrographis*) (25 μg/ml), Xanthohumol (1 μg/ml), Sulforaphane (3 μg/ml), *Withania* (20 μg/ml), I3C (25 μg/ml), Resveratrol (20 μg/ml), Milk Thistle (25 μg/ml), IAA (5 μg/ml), Pomegranite (25 μg/ml), Parthenolide (20 μg/ml), Amla (25 μg/ml), Oleanolic acid (25 μg/ml), DIM (25 μg/ml), Quercetin (20 μg/ml), Berberine (20 μg/ml), Cinnamon (25 μg/ml), Puerariae (20 μg/ml), *Wasabia* Rhizome (25 μg/ml), Watercress (25 μg/ml), *Epimedium* (20 μg/ml), chlorogenic acid (25 μg/ml), *Abelmoschus* (20 μg/ml), Bonistein (20 μg/ml), Peppermint (25 μg/ml), Blueberry (25 μg/ml), *Picrorhiza* (25 μg/ml), *Wasabia* Powder (25 μg/ml), HHIAA (5 μg/ml), Osteosine (20 μg/ml), Dandelion (25 μg/ml), Green Coffee (25 μg/ml) and THIAA (5 μg/ml).

TABLE 4

Screening of test compounds for GST enzyme activity in the RL-34 cell line

| Test Compound (ug/mL) | Fold Induction of GST activity | SEM | n |
|---|---|---|---|
| Sulforaphane (3 ug/mL) | 1.8 | 0.12 | 5 |
| *Andrographis* (25 ug/mL) | 1.4 | 0.03 | 4 |
| Xanthohumol (1 ug/mL) | 1.4 | 0.05 | 3 |
| Prune (20 ug/mL) | 1.4 | | 1 |
| Formula DF-SH (50 ug/mL) | 1.3 | 0.10 | 3 |
| *Withania* (20 ug/mL) | 1.3 | 0.02 | 2 |
| Osteosine (20 ug/mL) | 1.2 | | 1 |
| MCHA (20 ug/mL) | 1.2 | | 1 |
| Arthred Porcine (20 ug/mL) | 1.2 | | 1 |
| Glucosamine (20 ug/mL) | 1.1 | | 1 |
| Resveratrol (20 ug/mL) | 1.1 | 0.08 | 2 |
| CLA (20 ug/mL) | 1.1 | 0.03 | 2 |
| Dandelion (25 ug/mL) | 1.1 | 0.19 | 4 |
| I3C (25 ug/mL) | 1.1 | 0.08 | 2 |
| Black Cohosh (20 ug/mL) | 1.1 | 0.04 | 2 |
| Spent Hops (50 ug/mL) | 1.1 | 0.07 | 3 |
| IAA (5 ug/mL) | 1.1 | 0.05 | 4 |
| Vitamin C (20 ug/mL) | 1.1 | 0.01 | 2 |
| Ipriflavone (20 ug/mL) | 1.1 | 0.00 | 2 |
| chlorogenic acid (25 ug/mL) | 1.1 | | 1 |
| K-Citrate (20 ug/mL) | 1.1 | 0.04 | 2 |
| Hyaluronic acid (20 ug/mL) | 1.1 | | 1 |
| Arthred Bovine (20 ug/mL) | 1.0 | 0.01 | 2 |
| Cinnamon (25 ug/mL) | 1.0 | 0.01 | 2 |
| RIAA (5 ug/mL) | 1.0 | 0.00 | 2 |
| *Astragalus* (20 ug/mL) | 1.0 | | 1 |
| Broc 19 (25 ug/mL) | 1.0 | | 1 |
| Broc 49 (25 ug/mL) | 1.0 | | 1 |
| Bonistein (20 ug/mL) | 1.0 | | 1 |
| Broc 11 (25 ug/mL) | 1.0 | | 1 |
| Rutin (20 ug/mL) | 1.0 | 0.04 | 2 |
| *Perilla* (20 ug/mL) | 1.0 | 0.03 | 3 |
| Olive Oil (20 ug/mL) | 1.0 | 0.05 | 2 |
| Parthenolide (20 ug/mL) | 1.0 | 0.06 | 2 |
| HHIAA (5 ug/mL) | 1.0 | 0.01 | 3 |
| Quercitin (20 ug/mL) | 1.0 | 0.02 | 2 |
| *Terminalin* (25 ug/mL) | 1.0 | 0.03 | 2 |
| Pomegranite (25 ug/mL) | 1.0 | 0.04 | 3 |
| Oleanolic acid (25 ug/mL) | 1.0 | 0.01 | 4 |
| Flaxseed (20 ug/mL) | 1.0 | 0.07 | 2 |
| Curcumin (5 ug/mL) | 1.0 | 0.04 | 2 |
| Inulin (20 ug/mL) | 1.0 | 0.04 | 2 |
| *Epimedium* (20 ug/mL) | 1.0 | 0.09 | 2 |
| Blueberry (25 ug/mL) | 1.0 | 0.05 | 2 |
| Irish Moss (25 ug/mL) | 1.0 | 0.08 | 2 |
| Fructus LL (20 ug/mL) | 1.0 | 0.08 | 2 |
| FOS (20 ug/mL) | 1.0 | 0.05 | 2 |
| DIM (25 ug/mL) | 1.0 | 0.00 | 2 |
| Broc 13 (25 ug/mL) | 1.0 | | 1 |
| Puerariae (20 ug/mL) | 1.0 | 0.07 | 2 |
| THIAA (5 ug/mL) | 1.0 | 0.02 | 3 |
| Peppermint (25 ug/mL) | 1.0 | 0.05 | 2 |
| Alma (25 ug/mL) | 1.0 | 0.02 | 4 |
| Milk Basic Protein (20 ug/mL) | 1.0 | | 1 |
| Policosanol (20 ug/mL) | 1.0 | 0.05 | 2 |
| Milk Thistle (25 ug/mL) | 1.0 | 0.04 | 4 |
| Glabridin (20 ug/mL) | 1.0 | | 1 |
| *Wasabia* Powder (20 ug/mL) | 1.0 | 0.04 | 2 |
| Phloridzin (20 ug/mL) | 1.0 | 0.01 | 2 |
| Green Coffee (25 ug/mL) | 1.0 | 0.03 | 2 |
| Broc 12 (25 ug/mL) | 1.0 | | 1 |
| *Picrorhiza* (25 ug/mL) | 1.0 | 0.03 | 3 |
| Green Tea (25 ug/mL) | 1.0 | | 1 |
| Berberine (20 ug/mL) | 1.0 | | 1 |
| DHEA (20 ug/mL) | 1.0 | 0.01 | 2 |
| Broc 10 (25 ug/mL) | 1.0 | | 1 |
| Bonepep (20 ug/mL) | 1.0 | 0.01 | 2 |
| Broc 14 (25 ug/mL) | 1.0 | | 1 |
| Oleuropein (20 ug/mL) | 1.0 | 0.04 | 2 |
| Vitamin K2 (20 ug/mL) | 1.0 | | 1 |
| Garlic (25 ug/mL) | 1.0 | 0.06 | 2 |
| Devils Claw (20 ug/mL) | 1.0 | 0.12 | 2 |
| Kolla 2 (20 ug/mL) | 1.0 | 0.04 | 2 |
| *Wasabia* Rhizome (25 ug/mL) | 1.0 | 0.00 | 2 |
| Hesperidin (20 ug/mL) | 1.0 | 0.07 | 2 |
| Watercress (25 ug/mL) | 1.0 | 0.05 | 2 |
| *Dioscorea* (20 ug/mL) | 1.0 | 0.05 | 3 |
| DHA (20 ug/mL) | 1.0 | 0.03 | 2 |
| Black Tea (20 ug/mL) | 1.0 | 0.13 | 2 |
| *Salvia* MB (20 ug/mL) | 0.9 | 0.04 | 2 |
| *Abelmoschus* (20 ug/mL) | 0.9 | 0.10 | 2 |
| Soy Isoflavones (20 ug/mL) | 0.9 | 0.04 | 2 |
| Broc 09 (25 ug/mL) | 0.9 | | 1 |
| Black Rice (20 ug/mL) | 0.8 | 0.14 | 2 |
| Red Yeast Rice (20 ug/mL) | 0.8 | 0.09 | 2 |

Formula DF-SH is the combination of spent hops, (1,7-Bis (4-hydroxy-3-methoxyphenyl)hepta-1,6-diene-3,5-dione) (curcumin), (3-(2-(Decahydro-6-hydroxy-5-(hydroxymethyl)-5,8a-dimethyl-2-methylenenaphthyl)ethylidene)dihydro-4-hydroxyfuran-2(3H)-one) (*andrographis*), Rho Isoalpha acid and Zn (525:30:30:4:1)

TABLE 5

Screening of test compounds for NQO-1 enzyme activity in the RL-34 cell line

| Test Compound (ug/mL) | Induction of NQO1 activity | SEM | n |
|---|---|---|---|
| Curcumin (5 ug/mL) | 4.6 | 1.59 | 3 |
| *Andrographis* (25 ug/mL) | 4.5 | 1.00 | 4 |
| Formula DF-SH (50 ug/mL) | 4.0 | 0.43 | 3 |
| Xanthohumol (1 ug/mL) | 3.7 | 0.78 | 3 |
| Sulforaphane (3 ug/mL) | 3.7 | 0.76 | 4 |
| *Withania* (20 ug/mL) | 2.4 | 0.72 | 2 |
| I3C (25 ug/mL) | 2.4 | 0.34 | 2 |
| Resveratrol (20 ug/mL) | 2.2 | 0.44 | 2 |
| Spent Hops (50 ug/mL) | 2.0 | 0.15 | 3 |
| Milk Thistle (25 ug/mL) | 2.0 | 0.04 | 4 |
| IAA (5 ug/mL) | 1.9 | 0.16 | 4 |
| Pomegranite (25 ug/mL) | 1.8 | 0.41 | 3 |
| Parthenolide (20 ug/mL) | 1.7 | 0.25 | 2 |
| Alma (25 ug/mL) | 1.6 | 0.09 | 4 |
| Oleanolic acid (25 ug/mL) | 1.5 | 0.08 | 4 |
| DIM (25 ug/mL) | 1.5 | 0.22 | 2 |
| Quercitin (20 ug/mL) | 1.4 | 0.07 | 2 |
| Berberine (20 ug/mL) | 1.4 | 0.47 | 2 |
| Cinnamon (25 ug/mL) | 1.4 | 0.28 | 2 |
| *Puerariae* (20 ug/mL) | 1.4 | 0.06 | 2 |
| *Wasabia* Rhizome (25 ug/mL) | 1.4 | 0.17 | 2 |
| Watercress (25 ug/mL) | 1.3 | 0.03 | 2 |
| *Epimedium* (20 ug/mL) | 1.3 | | 1 |
| chlorogenic acid (25 ug/mL) | 1.2 | 0.02 | 2 |
| *Abelmoschus* (20 ug/mL) | 1.2 | 0.28 | 2 |
| Bonistein (20 ug/mL) | 1.2 | | 1 |
| Peppermint (25 ug/mL) | 1.2 | 0.09 | 4 |
| Blueberry (25 ug/mL) | 1.2 | 0.04 | 2 |
| *Picrorhiza* (25 ug/mL) | 1.2 | 0.03 | 2 |
| *Wasabia* Powder (25 ug/mL) | 1.2 | 0.03 | 2 |
| HHIAA (5 ug/mL) | 1.2 | 0.07 | 3 |
| Osteosine (20 ug/mL) | 1.2 | | 1 |
| Dandelion (25 ug/mL) | 1.2 | 0.01 | 2 |
| Green Coffee (25 ug/mL) | 1.2 | 0.01 | 2 |
| THIAA (5 ug/mL) | 1.2 | 0.08 | 3 |
| RIAA (5 ug/mL) | 1.1 | 0.01 | 2 |
| Irish Moss (25 ug/mL) | 1.1 | | 1 |
| Broc 10 (25 ug/mL) | 1.1 | | 1 |
| Broc 19 (25 ug/mL) | 1.1 | | 1 |
| Broc 49 (25 ug/mL) | 1.1 | | 1 |
| Black Rice (20 ug/mL) | 1.1 | 0.10 | 2 |
| Policosanol (20 ug/mL) | 1.1 | 0.06 | 2 |
| DHEA (20 ug/mL) | 1.1 | 0.11 | 2 |
| Broc 09 (25 ug/mL) | 1.1 | | 1 |
| Broc 12 (25 ug/mL) | 1.1 | | 1 |
| Broc 14 (25 ug/mL) | 1.1 | | 1 |
| Flaxseed (20 ug/mL) | 1.1 | 0.05 | 2 |
| Sly Isoflavones (20 ug/mL) | 1.1 | 0.02 | 2 |
| Arthred Porcine (20 ug/mL) | 1.1 | | 1 |
| Garlic (25 ug/mL) | 1.0 | | 1 |
| Hesperidin (20 ug/mL) | 1.0 | 0.04 | 2 |
| *Terminalin* (25 ug/mL) | 1.0 | 0.16 | 2 |
| Broc 11 (25 ug/mL) | 1.0 | | 1 |
| *Perilla* (20 ug/mL) | 1.0 | 0.05 | 2 |
| Prune (20 ug/mL) | 1.0 | | 1 |
| CLA (20 ug/mL) | 1.0 | 0.05 | 2 |
| *Salvia* MB (20 ug/mL) | 1.0 | 0.03 | 2 |
| MCHA (20 ug/mL) | 1.0 | | 1 |
| *Dioscorea* (20 ug/mL) | 1.0 | 0.12 | 2 |
| Oleuropein (20 ug/mL) | 1.0 | 0.02 | 2 |
| Broc 13 (25 ug/mL) | 1.0 | | 1 |
| Glabridin (20 ug/mL) | 1.0 | 0.02 | 2 |
| Arthred Bovine (20 ug/mL) | 1.0 | 0.13 | 3 |
| Black Cohosh (20 ug/mL) | 1.0 | 0.03 | 2 |
| Olive Oil (20 ug/mL) | 1.0 | 0.06 | 2 |
| Phloridzin (20 ug/mL) | 1.0 | 0.02 | 2 |
| Kolla 2 (20 ug/mL) | 1.0 | 0.04 | 2 |
| Glucosamine (20 ug/mL) | 1.0 | | 1 |
| *Astragalus* (20 ug/mL) | 1.0 | | 1 |
| DHA (20 ug/mL) | 0.9 | 0.03 | 2 |
| Hyaluronic acid (20 ug/mL) | 0.9 | | 1 |
| Inulin (20 ug/mL) | 0.9 | 0.03 | 2 |
| FOS (20 ug/mL) | 0.9 | 0.07 | 2 |
| Vitamin C (20 ug/mL) | 0.9 | | 1 |
| Bonepep (20 ug/mL) | 0.9 | | 1 |
| K-Citrate (20 ug/mL) | 0.9 | 0.05 | 2 |
| Black Tea (20 ug/mL) | 0.9 | 0.00 | 2 |
| Green Tea (25 ug/mL) | 0.9 | | 1 |
| Vitamin K2 (20 ug/mL) | 0.9 | 0.02 | 2 |
| Milk Basic Protein (20 ug/mL) | 0.9 | | 1 |
| Rutin (20 ug/mL) | 0.9 | 0.07 | 2 |
| Fructus LL (20 ug/mL) | 0.9 | 0.03 | 2 |
| Ipriflavone (20 ug/mL) | 0.8 | 0.02 | 2 |
| Red Yeast Rice (20 ug/mL) | 0.8 | 0.04 | 2 |
| Devils Claw (20 ug/mL) | 0.8 | 0.14 | 2 |

Formula DF-SH is the combination of spent hops, (1,7-Bis(4-hydroxy-3-methoxyphenyl)hepta-1,6-diene-3,5-dione) (curcumin), (3-(2-(Decahydro-6-hydroxy-5-(hydroxymethyl)-5,8a-dimethyl-2-methylenenaphthyl)ethylidene)dihydro-4-hydroxyfuran-2(3H)-one) (*andrographis*), Rho Isoalpha acid and Zn (525:30:30:4:1)

HO-1 Transcriptional activation—Heme oxygenase is regulated by both Nrf-2 and MTF-1 transcriptional factors through the activation of ARE and MRE binding sites on heme oxygenase gene. Sulforaphane, a known compound for the activation of Nrf-2 transcriptional factor induces the heme oxygenase promoter activity in the HepG2 cell line (Table 6). Thirty percent induction of the activity by test compounds over DMSO control is considered as active. Test compounds (1,7-Bis(4-hydroxy-3-methoxyphenyl)hepta-1,6-diene-3,5-dione) (curcumin), xanthohumol, (3-(2-(Decahydro-6-hydroxy-5-(hydroxymethyl)-5,8a-dimethyl-2-methylenenaphthyl)ethylidene)dihydro-4-hydroxyfuran-2(3H)-one) (*andrographis*) extract, sulforaphane, IAA, oleanolic acid, green tea catechins, milk thistle, terminalin, $ZnCl_2$, garlic, amla fruit extract and cinnamon ground induced the expression of heme oxygenase promoter activity.

TABLE 6

Activation of the heme oxygenase (HO-1) luciferase reporter by test compounds in the HepG2 cell line

| Test compounds | Activity | ±SEM |
|---|---|---|
| Curcumin | 6.1 | +/−2.55 |
| Xanthohumol | 5.4 | +/−0.64 |
| *Andrographis* Extract | 4.4 | +/−0.57 |
| Sulforaphane | 4.2 | +/−0.70 |
| IAA | 3.6 | +/−0.85 |
| Oleanolic Acid | 2.7 | +/−1.20 |
| Green Tea catechins | 2.6 | +/−0.49 |
| Milk Thistle | 2.0 | +/−0.28 |
| Terminalin | 1.7 | +/−0.01 |
| ZnCl2 | 1.5 | +/−0.01 |
| Garlic | 1.4 | +/−0.01 |
| Amla Fruit extract | 1.3 | +/−0.50 |
| Cinnamon ground | 1.3 | +/−0.01 |

Gene Expression—The relative expression (RE) of the genes analyzed was reported relative to GAPDH. To determine the relative expression to the control cells, the ratio of treatment to the DMSO control average RE value was calculated for all samples. The average of hMT1&2 and hMT1&2alt was calculated and expressed as MT 1, 2. The average of GSTA1 and NQO1 was calculated and expressed as Phase II gene induction. The average gene expression for metallothionein (MT 1, 2), heme oxygenase (HMOX1), and phase II enzymes (GSTA1 and NQO1) is seen in Table 7. As a control, CdCl$_2$, was shown to induce both MT and HMOX1, however was unable to increase phase II. Alternatively, sulforaphane increased phase II and HMOX1, but not MT. Test compounds that increased≧20% (in rank order) phase II include *andrographis*, IAA and curcumin; HMOX1 include curcumin, *andrographis*, fucus mesh, gymnogongrus, IAA, and xanthohumol; MT include oleanolic acid, fucus mesh, xanthohumol and gymnogongrus.

after 4 hours. As a control, sulforaphane displayed a dramatic increase in Nrf-2 nuclear translocation. The combination of spent hops, (1,7-Bis(4-hydroxy-3-methoxyphenyl)hepta-1, 6-diene-3,5-dione) (curcumin), (3-(2-(Decahydro-6-hydroxy-5-(hydroxymethyl)-5,8a-dimethyl-2-methylenenaphthyl)ethylidene)dihydro-4-hydroxyfuran-2(3H)-one) (*andrographis*), Rho Isoalpha acid and Zn (525:30:30:4:1) and IAA, (1,7-Bis(4-hydroxy-3-methoxyphenyl)hepta-1,6-diene-3,5-dione) (curcumin), (3-(2-(Decahydro-6-hydroxy-5-(hydroxymethyl)-5,8a-dimethyl-2-methylenenaphthyl) ethylidene)dihydro-4-hydroxyfuran-2(3H)-one) (*andrographis*) (1:1:1) also showed a marked translocation of Nrf-2 to the nucleus.

TABLE 7

Gene expression in HepG2 cells following treatment with test compounds (values shown are µg/ml)

|  | MT 1,2 (ave) | | HMOX1 | | Phase II (ave) | |
| --- | --- | --- | --- | --- | --- | --- |
|  | Ratio to DMSO | +/−SD | Ratio to DMSO | +/−SD | Ratio to DMSO | +/−SD |
| DMSO Control | 1.00 | 0.26 | 1.00 | 0.15 | 1.00 | 0.09 |
| CdCl2 (40 uM) | 83.31 | 18.50 | 21.23 | 5.28 | 0.94 | 0.23 |
| Sulforaphane (3) | 0.67 | 0.16 | 8.82 | 1.98 | 1.84 | 0.44 |
| *Andrographis* (25) | 0.87 | 0.12 | 2.43 | 0.37 | 2.29 | 0.39 |
| Curcumin (5) | 0.90 | 0.48 | 2.09 | 1.14 | 1.15 | 0.43 |
| ZnCl2 (10) | 12.43 | 8.98 | 0.97 | 0.16 | 0.94 | 0.09 |
| IAA (5) | 0.89 | 0.12 | 1.26 | 0.15 | 1.26 | 0.18 |
| RIAA (5) | 0.83 | 0.22 | 2.54 | 1.82 | 1.15 | 0.35 |
| THIAA (5) | 0.90 | 0.17 | 1.11 | 0.01 | 0.99 | 0.13 |
| Xanthohumol (1) | 0.90 | 0.40 | 1.11 | 0.12 | 1.02 | 0.19 |
| Spent Hops (20) | 1.35 | 0.31 | 1.31 | 0.15 | 0.69 | 0.29 |
| Spent Hops (50) | 2.12 | 0.61 | 1.25 | 0.08 | 1.14 | 0.64 |
| SH formula (10) | 0.95 | 0.13 | 1.64 | 0.20 | 1.06 | 0.07 |
| SH formula (20) | 1.04 | 0.13 | 3.55 | 0.15 | 1.52 | 0.07 |
| SH formula (50) | 0.79 | 0.30 | 1.14 | 0.12 | 0.66 | 0.09 |
| 3C formula (1) | 1.15 | 0.14 | 0.85 | 0.12 | 0.84 | 0.16 |
| 3C formula (2.5) | 1.05 | 0.11 | 1.03 | 0.05 | 1.00 | 0.20 |
| 3C formula (5) | 2.07 | 2.00 | 30.34 | 49.01 | 29.93 | 59.01 |
| 3C formula (7.5) | 1.12 | 0.11 | 2.14 | 0.33 | 11.12 | 21.07 |
| Oleanolic (25) | 2.39 | 0.52 | 1.88 | 1.41 | 0.91 | 0.27 |
| *Withania* (20) | 1.06 | 0.18 | 1.17 | 0.23 | 0.98 | 0.24 |
| As. Nod Mesh (25) | 1.05 | 0.08 | 0.82 | 0.02 | 0.68 | 0.16 |
| *C. Chamissoi* (25) | 1.01 | 0.07 | 1.04 | 0.13 | 0.86 | 0.15 |
| *C. Crispus* (25) | 1.07 | 0.18 | 0.90 | 0.20 | 0.79 | 0.16 |
| Fucus Mesh (25) | 1.28 | 0.18 | 2.12 | 1.37 | 6.82 | 11.77 |
| Green Tea (25) | 0.85 | 0.09 | 0.77 | 0.00 | 0.83 | 0.11 |
| Gymnogongrus (25) | 1.19 | 0.03 | 1.63 | 0.89 | 0.97 | 0.02 |
| Irish Moss (25) | 2.07 | 2.26 | 0.91 | 0.07 | 0.91 | 0.07 |
| *Sarcodiotheca* (25) | 0.88 | 0.09 | 0.85 | 0.15 | 0.77 | 0.08 |

Figure 3:
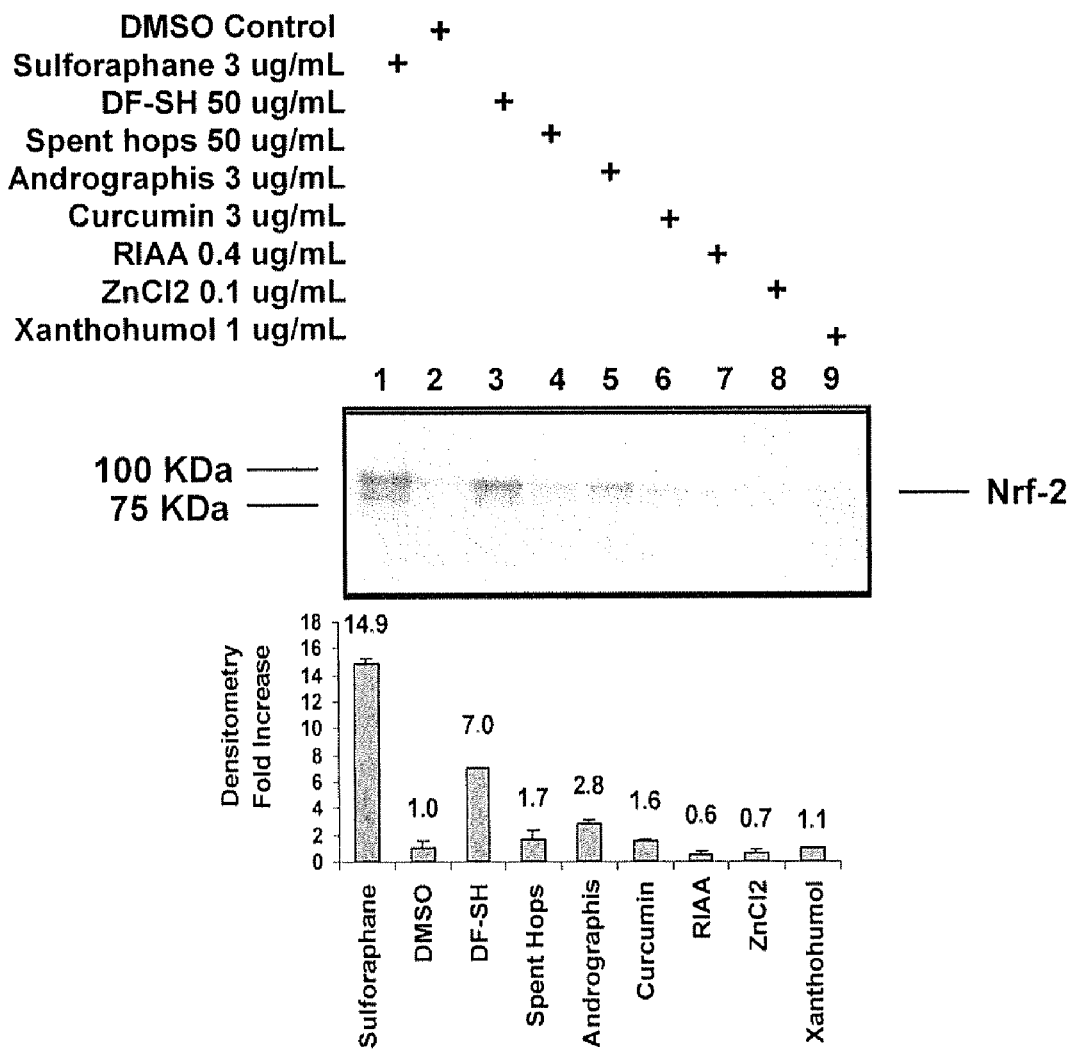
FIG. 3 depicts a Western blot analysis of Nrf-2 in the nuclear fraction of HepG2 cells treated for 4 hours with the indicated test compound. Formula DF-SH is the combination of spent hops, 7-Bis(4-hydroxy-3-methoxyphenyl)hepta-1,6-diene-3,5-dione (curcumin), 3-(2-(Decahydro-6-hydroxy-5-(hydroxymethyl)-5,8a-dimethyl-2-methylenenaphthyl)ethylidene)dihydro-4-hydroxyfuran-2(3H)-one (*andrographis*), Rho dyhdro-isoalpha acids (RIAA) mixture and Zn (525:30: 30:4:1).
Figure 4:
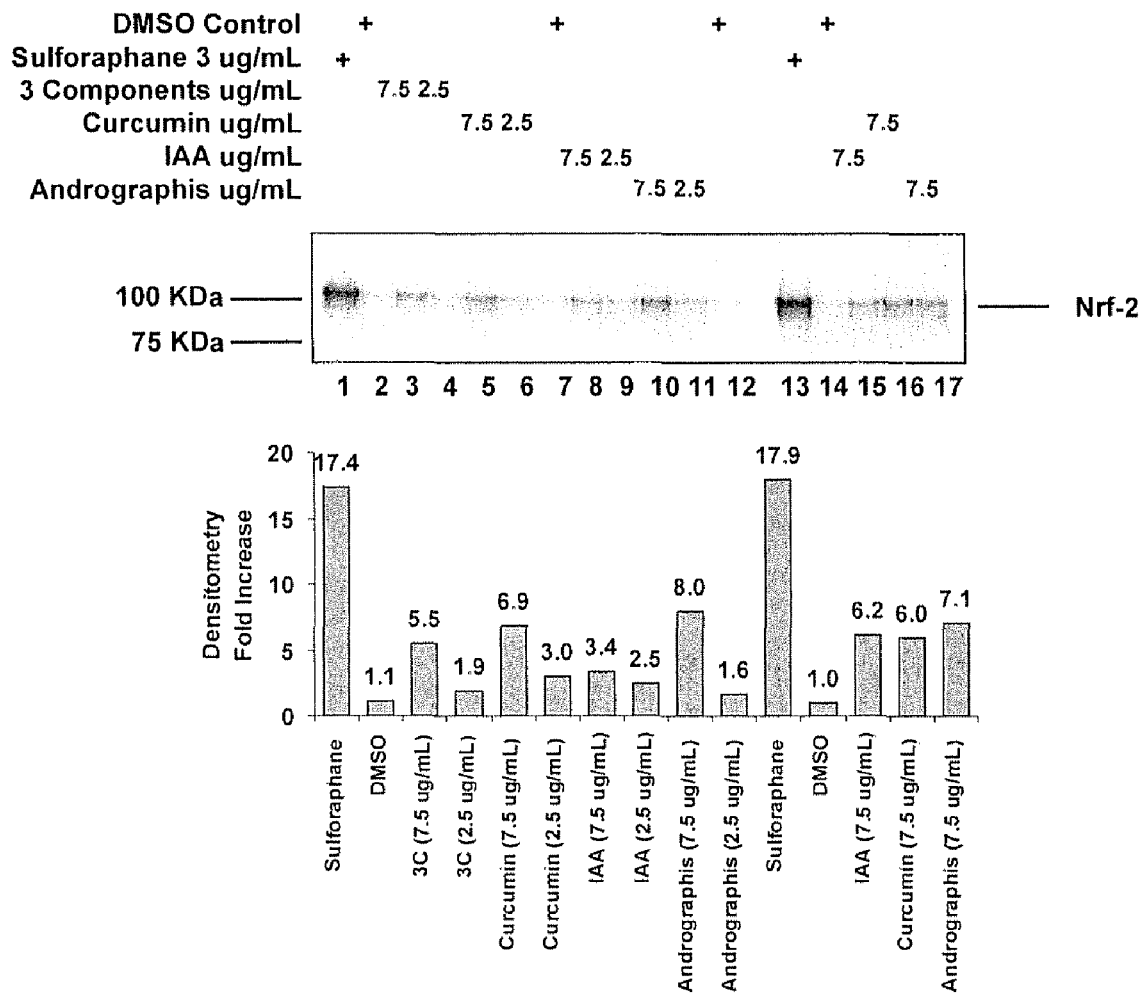
FIG. 4 depicts a Western blot analysis of Nrf-2 in the nuclear fraction of HepG2 cells treated for 4 hours with the indicated test compound. Formula 3 Components is the combination of Isoalpha acid (IAA), 7-Bis(4-hydroxy-3-methoxyphenyl)hepta-1,6-diene-3,5-dione (curcumin), and 3-(2-(Decahydro-6-hydroxy-5-(hydroxymethyl)-5,8a-dimethyl-2-methylenenaphthyl)ethylidene)dihydro-4-hydroxyfuran-2 (3H)-one (*andrographis*), (1:1:1).

3C formula is the combination of equal ratios of IAA, (1,7-Bis(4-hydroxy-3-methoxyphenyl)hepta-1,6-diene-3,5-dione) (curcumin), and (3-(2-(Decahydro-6-hydroxy-5-(hydroxymethyl)-5,8a-dimethyl-2-methylenenaphthyl)ethylidene)dihydro-4-hydroxyfuran-2(3H)-one) (*andrographis*). SH formula is the combination of spent hops, Rho Isoalpha acid, (1,7-Bis(4-hydroxy-3-methoxyphenyl) hepta-1,6-diene-3,5-dione) (curcumin), (3-(2-(Decahydro-6-hydroxy-5-(hydroxymethyl)-5,8a-dimethyl-2-methylenenaphthyl)ethylidene)dihydro-4-hydroxyfuran-2(3H)-one) (*andrographis*), and zinc (525:4:30:30:1). The gray shading indicates only one replicate Nrf-2 Translocation—The translocation of Nrf-2 from the cytoplasm to the nucleus has been shown to occur with treatment of xenobiotics and antioxidants (Chan, J. Y. and M. Kwong, Biochim Biophys Acta, 1517(1): 19-26, 2000, and Chan, K., et al., Proc Natl Acad Sci USA, 93(24): 13943-8, 1996). As seen in FIGS. 3 and 4, Nrf-2 was observed in the nuclear fraction of HepG2 cells treated with test compound Example 2

Effects of Test Formulation on Metallothionein mRNA Production

This experiment was a study investigating the effects of a unique nutraceutical combination upon biomarkers of metal detoxification and elimination.

Nine volunteers were recruited and followed for 14 days. Baseline evaluations were obtained at Visit 1. Treatment with a test formulation comprising (per tablet): zinc (1.667 mg); 3-(2-(Decahydro-6-hydroxy-5-(hydroxymethyl)-5,8a-dimethyl-2-methylenenaphthyl)ethylidene)dihydro-4-hydroxyfuran-2(3H)-one (50 mg); 1,7-Bis(4-hydroxy-3-methoxyphenyl)hepta-1,6-diene-3,5-dione (50 mg); spent hops (875 mg) and a Rho dihydro-isoalpha acid mixture (6.667 mg) was begun immediately thereafter and continued for 10 days.

Clinical evaluations were made at Visit 2 (Day 3), Visit 3 (Day 6), Visit 4 (Day 8), Visit 5 (Day 10), and Visit 6 (Day 14).

Visit 6 occurred 4 days after discontinuation of treatment. Basic safety labs at visits 1 and 5 were obtained including complete blood counts, comprehensive metabolic panels and gamma glutamyl transferase levels. Efficacy endpoints included messenger RNA levels of Metallothionein 1 and 2 (reflecting gene up-regulation) and unprovoked urinary excretion of toxic and nutrient trace elements.

Metallothionein mRNA measurements estimations in human blood samples were performed as follows:

RNA Extraction—After collection, 2 ml whole blood was mixed with 5 ml of RNAlater (Ambion, Austin, Tex.). RNA extractions were performed with the RiboPure Blood RNA Isolation Kit (Ambion, Austin, Tex.) according to the manufacturers specifications. RNA was quantified with a Nanodrop spectrophotometer (Nanodrop Technologies, Wilmington, Del.).

Reverse Transcriptase Assays—RNA was converted to first strand cDNA by use of the RETROscript First Strand Synthesis Kit (Ambion, Austin, Tex.) and primed with oligo-dT according to the manufacturers specifications.

Primers and Probes—A Taqman gene expression assay to quantify GAPDH expression, which was used as an endogenous control, was obtained from Applied Biosystems (Foster City, Calif.; assay Hs99999905_m1). Primers and probes for Taqman-based assays targeting human metallothioneins have been previously described (Aydemir T B, Blanchard R K, and Cousins R J, 2006. Zinc supplementation of young men alters metallothionein, zinc transporter, and cytokine gene expression in leukocyte populations. Proc. Natl. Acad. Sci. USA 103, 1699-1704). Forward and reverse primers, and HPLC-purified Taqman probes labeled with 5'-FAM and 3'-TAMRA, were obtained from Operon Biotechnologies, Inc (Huntsville, Ala.).

The sequences of these reagents are shown below.

```
hMT1,2-F      5'-GCACCTCCTGCAAGAAAAGCT
hMT1,2-R      5'-GCAGCCTTGGGCACACTT
hMT1,2-T      5'-FAM CACAGCCCACACGGGCAGCAGG TAMRA
hMT1,2Alt-F   5'-GCACCTCCTGCAAGAAGAGCT
hMT1,2Alt-R   5'-GCAGCCCTGGGCACACTT
hMT1,2Alt-T   5'-FAM ACAGCCCACAGGACAGCAGG
```

Quantitative PCR Assays—Two-step Taqman-based RT-qPCR was performed. First strand cDNA was synthesized as described above. In the first experiment, the cDNA equivalent of 20 ng starting RNA was then included in qPCR reactions. Reactions to detect metallothionein expression contained 1× Taqman Master Mix (Applied Biosystems, Foster City, Calif.), forward and reverse primers at 400 nM, and Taqman probe at 200 nM. Reactions to detect GAPDH expression contained 1× Taqman Master Mix (Applied Biosystems) and 1× gene-specific assay reagents as recommended by the manufacturer (Applied Biosystems). All reactions were run in triplicate. Reactions that did not contain template cDNA were included as negative controls. In a second experiment with a subset of the samples, the cDNA equivalent of 100 ng starting RNA was included in qPCRs with the other conditions as described above. A reference sample was included in both assays to allow cross-assay comparison.

Reaction plates were processed on an Applied Biosystems 7900HT Sequence Detection System. The AmpliTaq Gold polymerase was activated at 95° C. for 10 min followed by 40 cycles consisting of denaturation for 15 seconds at 95° C. and annealing and extension for 60 seconds at 60° C.

Amplification data was analyzed with the ABI Prism SDS 2.1 software (Applied Biosystems). Relative quantification of gene expression was performed by the ΔΔCt method (Winer J, Jung C K S, Shackel I, Williams, P M. 1999. Development and validation of real-time quantitative reverse transcriptase-polymerase chain reaction for monitoring gene expression in cardiac myocytes in vitro. Anal Biochem. 270, 41-49), with GAPDH expression serving as an endogenous control to normalize expression within each sample.

Figure 5:
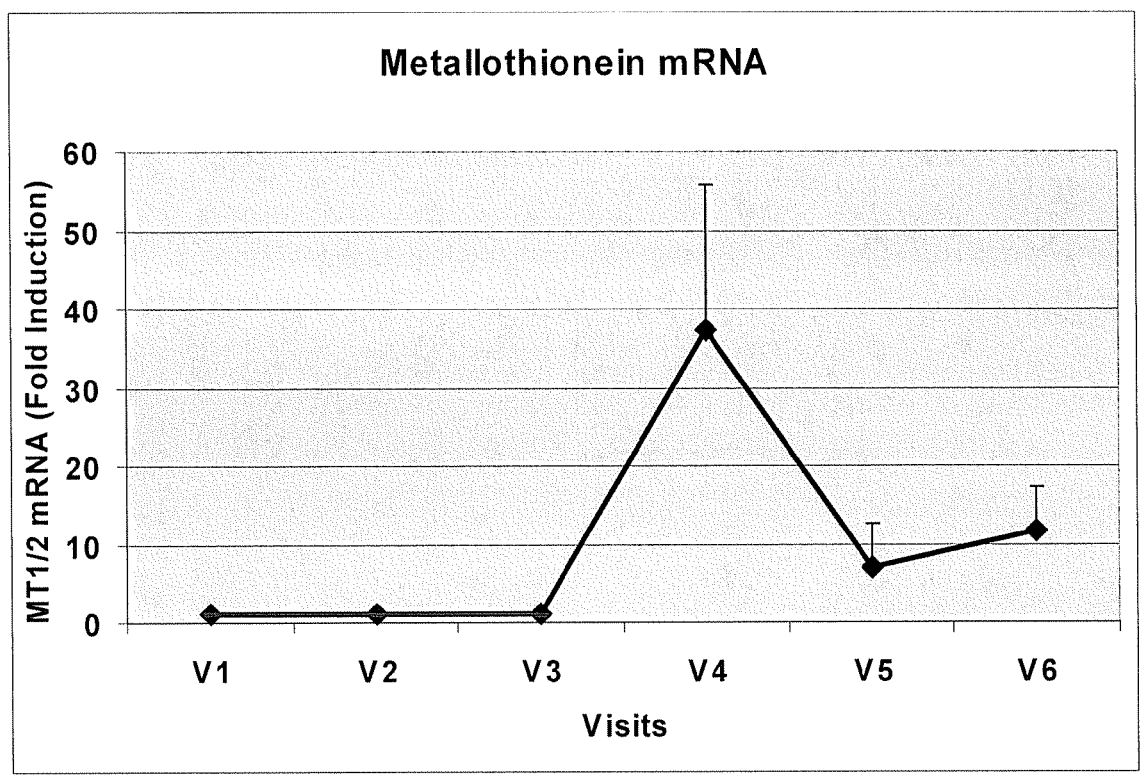
FIG. 5 graphically depicts the increased induction of metallothionein mRNA levels in volunteers following administration of a test formulation comprising (per tablet): zinc (1.667 mg); 3-(2-(Decahydro-6-hydroxy-5-(hydroxymethyl)-5,8a-dimethyl-2-methylenenaphthyl)ethylidene)dihydro-4-hydroxyfuran-2(3H)-one (50 mg); 1,7-Bis(4-hydroxy-3-methoxyphenyl)hepta-1,6-diene-3,5-dione (50 mg); spent hops (875 mg) and a Rho dihydro-isoalpha acid mixture (6.667 mg).
Figure 6:
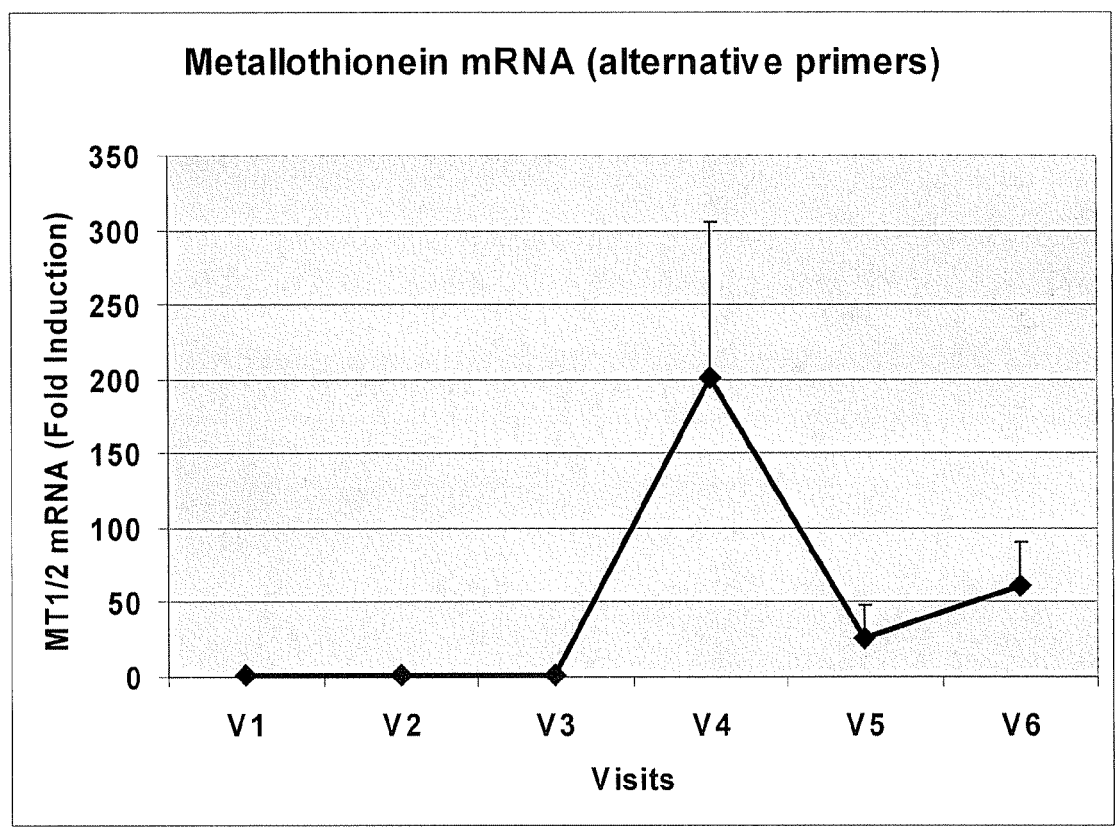
FIG. 6 graphically depicts the increased induction of metallothionein mRNA levels measured using alternative primers in volunteers following administration of a test formulation comprising (per tablet): zinc (1.667 mg); 3-(2-(Decahydro-6-hydroxy-5-(hydroxymethyl)-5,8a-dimethyl-2-methylenenaphthyl)ethylidene)dihydro-4-hydroxyfuran-2(3H)-one (50 mg); 1,7-Bis(4-hydroxy-3-methoxyphenyl)hepta-1,6-diene-3,5-dione (50 mg); spent hops (875 mg) and a Rho dihydro-isoalpha acid mixture (6.667 mg).

Results are depicted graphically in FIGS. 5 and 6 demonstrating the efficacy of the intervention in increasing measures of hepatic detoxification metallothionein mRNA levels.

Example 3

Effects of Test Formulation on Urinary Excretion of Heavy Metals

This study was conducted to determine the effects of a test formulation on urinary excretion of heavy metals in human volunteers.

Study Design—The study group and treatment regimen were as described in Example 2 above. Urine samples were collected and heavy metal determination performed by Genova Diagnostics, North Carolina, USA according to their in house procedures.

Figure 7:
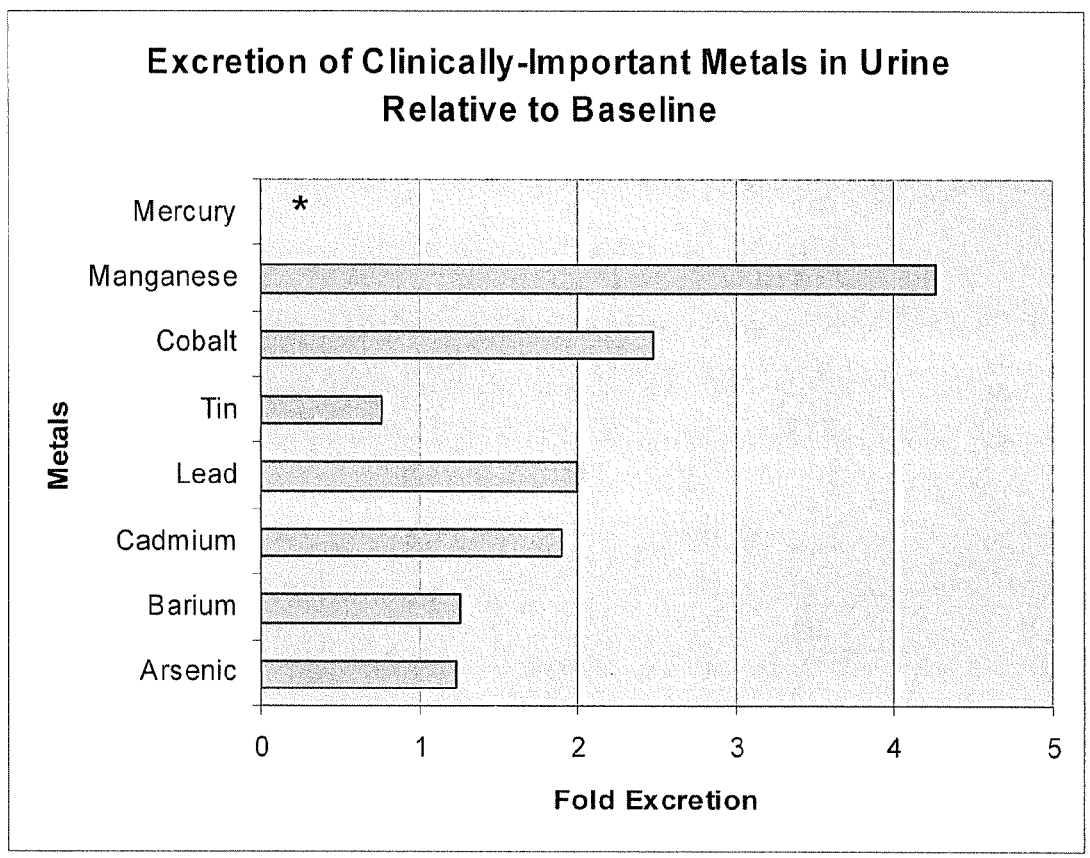
FIG. 7 graphically depicts the effects of test formulation on urinary excretion of clinically important metals. * denotes a detectable increase in excretion.
Figure 8:
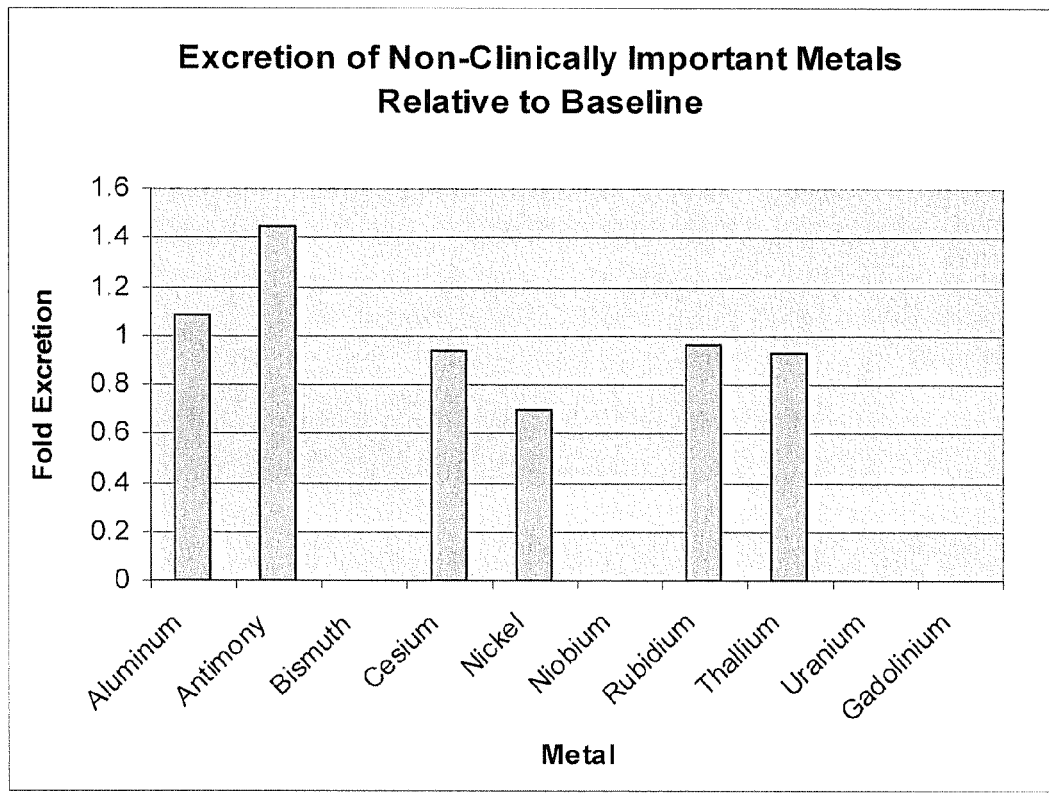
FIG. 8 graphically depicts the effects of test formulation on urinary excretion of non-clinically important metals.
Figure 9:
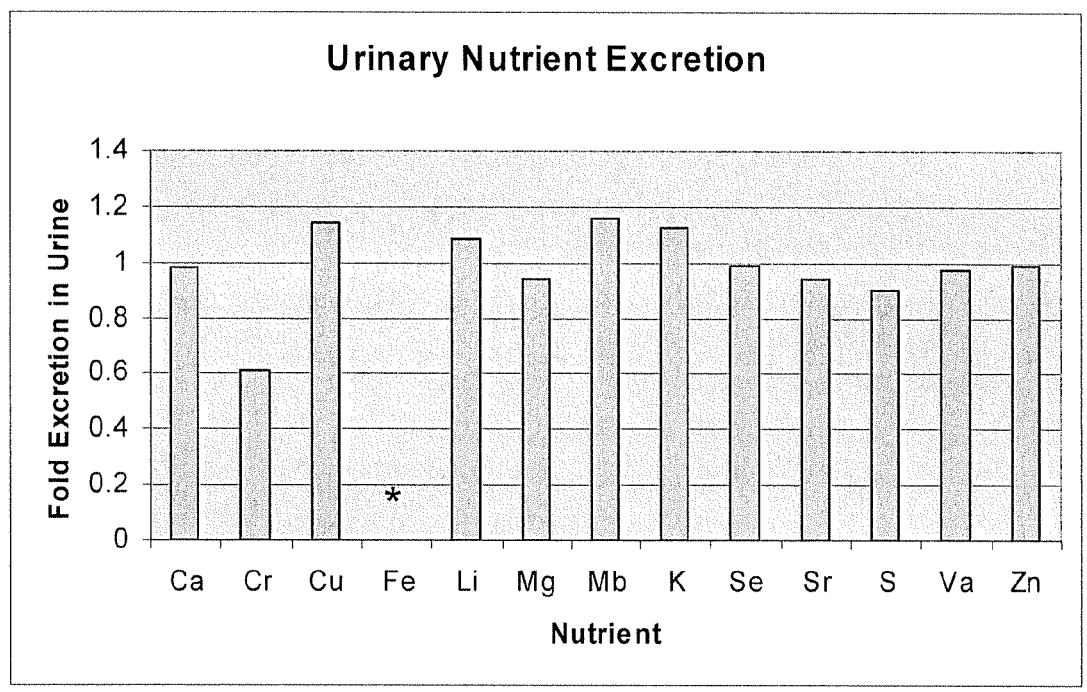
FIG. 9 graphically depicts the effects of test formulation on urinary excretion of nutrients. * denotes a detectable increase in excretion.

Results—Table 8 reports on the elimination of clinically relevant trace elements in test volunteers. FIGS. 7 and 8 graphically display the results of a test formulation on the excretion of clinically important (FIG. 7) and non-clinically important metals (FIG. 8). As can be seen in FIG. 7, the test formulation significantly promoted excretion of a number of important metals. FIG. 9 graphically displays the results of the test formulation on nutrient excretion in the urine.

TABLE 8

Urinary Excretion of Heavy Metals

| Metal | V1 avg* | V5 avg | % Change | Metal | V1 avg | V5 avg | % Change |
|---|---|---|---|---|---|---|---|
| Aluminum | 10.41 | 11.29 | 8.4 | Manganese | 0.51 | 2.17 | 327.0 |
| Antimony | 0.061 | 0.063 | 4.1 | Mercury | ND | ND | |
| Arsenic | 17.25 | 21.36 | 23.9 | Molybdenum | 39.5 | 45.75 | 15.8 |
| Barium | 2.35 | 2.95 | 25.5 | Nickle | 1.3883 | 1.4867 | 7.1 |
| Bismuth | ND | ND | | Niobium | ND | ND | |
| Cadmium | 0.16 | 0.30 | 90.5 | Platinum | 1.256 | 0.087 | −93.1*** |
| Calcium | 93.13 | 93.38 | −1.9 | Potassium | 2307.13 | 2594.38 | 12.5 |
| Cesium | 5.33 | 5.01 | −5.9 | Rubidium | 1831.38 | 1758.38 | −4.0 |
| Chromium | 2.25 | 1.38 | −38.9 | Selenium | 89.75 | 89.00 | −0.8 |

TABLE 8-continued

Urinary Excretion of Heavy Metals

| Metal | V1 avg* | V5 avg | % Change | Metal | V1 avg | V5 avg | % Change |
|---|---|---|---|---|---|---|---|
| Cobalt | 0.12 | 0.30 | 148.4 | Strontium | 101.75 | 96.00 | −5.7 |
| Copper | 8.29 | 9.46 | 14.2 | Sulfur | 519.38 | 466.38 | −10.2 |
| Creatinine | 43.12** | 58.86 | 36.5 | Thallium | 0.31 | 0.29 | −6.9 |
| Gadolinium | ND | ND | | Thorium | ND | ND | |
| Gallium | 0.033 | 0.059 | 80.0 | Tin | 2.19 | 1.68 | −23.3 |
| Iron | ND | ND | | Tungsten | ND | ND | |
| Lead | 0.35 | 0.617 | 76.2 | Uranium | ND | ND | |
| Lithium | 22.50 | 24.50 | 8.9 | Vanadium | 1.10 | 1.08 | −2.3 |
| Magnesium | 54.13 | 51.00 | −5.8 | Zinc | 330.5 | 326.0 | −1.4 |

*= amounts reported are in µg/g creatinine unless otherwise noted.
**= reported as mg/dL
***= data presented only for subjects with detectable levels of metal
ND = below detectable limits.

The invention claimed is:

1. A composition for promoting heavy metal detoxification in a mammal in need thereof, said composition comprising (a) from about 0.10 to about 10.00 grams of spent hops; (b) from about 5 to about 1200 mg of 1,7-Bis(4-hydroxy-3-methoxyphenyl)hepta-1,6-diene-3,5-dione; (c) from about 0.10 to about 24 mg of zinc; and (d) from about 5 to about 1200 mg of 3-(2-(Decahydro-6-hydroxy-5-(hydroxymethyl)-5,8a-dimethyl-2-methylenenaphthyl)ethylidene)dihydro-4-hydroxyfuran-2(3H)-one.

2. The composition according to claim 1, wherein the composition further comprises a compound selected from the group consisting of (4S,5S)-3,4-dihydroxy-4-[(1S)-hydroxy-4-methylpent-3-en-1-yl]-2-(3-methyl-butanoyl)-5-(3-methylbut-2-en-1-yl)cyclopent-2-en-1-one; (4R,5R)-3,4-dihydroxy-4-[(1R)-hydroxy-4-methylpent-3-en-1-yl]-2-(3-methyl-butanoyl)-5-(3-methylbut-2-en-1-yl)cyclopent-2-en-1-one; (4R,5R)-3,4-dihydroxy-4-[(1R)-hydroxy-4-methylpent-3-en-1-yl]-2-(2-methyl-butanoyl)-5-(3-methylbut-2-en-1-yl)cyclopent-2-en-1-one; (4R,5R)-3,4-dihydroxy-4-[(1R)-hydroxy-4-methylpent-3-en-1-yl]-5-(3-methyl-but-2-en-1-yl)-2-(2-methylpropanoyl)cyclopent-2-en-1-one; (4R,5R)-3,4-dihydroxy-4-[(1S)-hydroxy-4-methylpent-3-en-1-yl]-2-(3-methyl-butanoyl)-5-(3-methylbut-2-en-1-yl)cyclopent-2-en-1-one; (4R,5R)-3,4-dihydroxy-4-[(1S)-hydroxy-4-methylpent-3-en-1-yl]-2-(2-methyl-butanoyl)-5-(3-methylbut-2-en-1-yl)cyclopent-2-en-1-one; (4R,5R)-3,4-dihydroxy-4-[(1S)-hydroxy-4-methylpent-3-en-1-yl]-5-(3-methyl-but-2-en-1-yl)-2-(2-methylpropanoyl)cyclopent-2-en-1-one; (4R,5S)-3,4-dihydroxy-4-[(1R)-hydroxy-4-methylpent-3-en-1-yl]-2-(3-methyl-butanoyl)-5-(3-methylbut-2-en-1-yl)cyclopent-2-en-1-one; (4R,5S)-3,4-dihydroxy-4-[(1R)-hydroxy-4-methylpent-3-en-1-yl]-2-(2-methyl-butanoyl)-5-(3-methylbut-2-en-1-yl)cyclopent-2-en-1-one; (4R,5S)-3,4-dihydroxy-4-[(1R)-hydroxy-4-methylpent-3-en-1-yl]-5-(3-methyl-but-2-en-1-yl)-2-(2-methylpropanoyl)cyclopent-2-en-1-one; (4R,5S)-3,4-dihydroxy-4-[(1S)-hydroxy-4-methylpent-3-en-1-yl]-2-(3-methyl-butanoyl)-5-(3-methylbut-2-en-1-yl)cyclopent-2-en-1-one; (4R,5S)-3,4-dihydroxy-4-[(1S)-hydroxy-4-methylpent-3-en-1-yl]-2-(2-methyl-butanoyl)-5-(3-methylbut-2-en-1-yl)cyclopent-2-en-1-one; (4S,5R)-3,4-dihydroxy-4-[(1S)-hydroxy-4-methylpent-3-en-1-yl]-5-(3-methyl-but-2-en-1-yl)-2-(2-methylpropanoyl)cyclopent-2-en-1-one; (4S,5R)-3,4-dihydroxy-4-[(1S)-hydroxy-4-methylpent-3-en-1-yl]-2-(3-methyl-butanoyl)-5-(3-methylbut-2-en-1-yl)cyclopent-2-en-1-one; (4S,5R)-3,4-dihydroxy-4-[(1S)-hydroxy-4-methylpent-3-en-1-yl]-2-(2-methyl-propanoyl)-5-(3-methylbut-2-en-1-yl)cyclopent-2-en-1-one; (4S,5R)-3,4-dihydroxy-4-[(1S)-hydroxy-4-methylpent-3-en-1-yl]-2-(2-methyl-butanoyl)-5-(3-methylbut-2-en-1-yl)cyclopent-2-en-1-one; (4S,5S)-3,4-dihydroxy-4-[(1R)-hydroxy-4-methylpent-3-en-1-yl]-2-(3-methyl-butanoyl)-5-(3-methylbut-2-en-1-yl)cyclopent-2-en-1-one; (4S,5S)-3,4-dihydroxy-4-[(1R)-hydroxy-4-methylpent-3-en-1-yl]-2-(2-methyl-butanoyl)-5-(3-methylbut-2-en-1-yl)cyclopent-2-en-1-one; (4S,5S)-3,4-dihydroxy-4-[(1R)-hydroxy-4-methylpent-3-en-1-yl]-5-(3-methyl-but-2-en-1-yl)-2-(2-methylpropanoyl)cyclopent-2-en-1-one; (4S,5S)-3,4-dihydroxy-4-[(1S)-hydroxy-4-methylpent-3-en-1-yl]-2-(2-methyl-butanoyl)-5-(3-methylbut-2-en-1-yl)cyclopent-2-en-1-one; and (4S,5S)-3,4-dihydroxy-4-[(1S)-hydroxy-4-methylpent-3-en-1-yl]-5-(3-methyl-but-2-en-1-yl)-2-(2-methylpropanoyl)cyclopent-2-en-1-one.

3. The composition according to claim 1, wherein the composition further comprises a compound selected from the group consisting of (4R,5S)-3,4-dihydroxy-2-(3-methylbutanoyl)-5-(3-methylbutyl)-4-(4-methylpentanoyl)cyclopent-2-en-1-one; (4S,5S)-3,4-dihydroxy-2-(3-methylbutanoyl)-5-(3-methylbutyl)-4-(4-methylpentanoyl)cyclopent-2-en-1-one; (4S,5R)-3,4-dihydroxy-2-(3-methylbutanoyl)-5-(3-methylbutyl)-4-(4-methylpentanoyl)cyclopent-2-en-1-one; (4R,5R)-3,4-dihydroxy-2-(3-methylbutanoyl)-5-(3-methylbutyl)-4-(4-methylpentanoyl)cyclopent-2-en-1-one; (4R,5S)-3,4-dihydroxy-5-(3-methylbutyl)-4-(4-methylpentanoyl)-2-(3-methylpropanoyl)cyclopent-2-en-1-one; (4S,5S)-3,4-dihydroxy-5-(3-methylbutyl)-4-(4-methylpentanoyl)-2-(3-methylpropanoyl)cyclopent-2-en-1-one; (4S,5R)-3,4-dihydroxy-5-(3-methylbutyl)-4-(4-methylpentanoyl)-2-(3-methylpropanoyl)cyclopent-2-en-1-one; (4R,5R)-3,4-dihydroxy-5-(3-methylbutyl)-4-(4-methylpentanoyl)-2-(3-methylpropanoyl)cyclopent-2-en-1-one; 5S)-3,4-dihydroxy-2-(2-methylbutanoyl)-5-(3-methylbutyl)-4-(4-methylpentanoyl)cyclopent-2-en-1-one; (4S,5S)-3,4-dihydroxy-2-(2-methylbutanoyl)-5-(3-methylbutyl)-4-(4-methylpentanoyl)cyclopent-2-en-1-one; (4S,5R)-3,4-dihydroxy-2-(2-methylbutanoyl)-5-(3-methylbutyl)-4-(4-methylpentanoyl)cyclopent-2-en-1-one; and 5R)-3, 4-dihydroxy-2-(2-methylbutanoyl)-5-(3-methylbutyl)-4-(4-methylpentanoyl)cyclopent-2-en-1-one.

4. The composition according to claim 1, wherein the composition further comprises a compound selected from the group consisting of (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; and (4S,5S)-3,4-dihydroxy-4-[(1S)-1-hydroxy-4-methylpentyl]-2-(3-methylbutanoyl)-5-(3-methylbutyl)cyclopent-2-en-1-one.

5. The composition according to claim 1, wherein the composition further comprises a pharmaceutically acceptable excipient selected from the group consisting of coatings, isotonic and absorption delaying agents, binders, adhesives, lubricants, disintergrants, coloring agents, flavoring agents, sweetening agents, absorbants, detergents, and emulsifying agents.

6. The composition according to claim 1, wherein the composition further comprises one or more members selected from the group consisting of antioxidants, vitamins, minerals, proteins, fats, and carbohydrates.

7. A method for promoting heavy metal detoxification in a mammal in need thereof comprising administering to the mammal a composition comprising (a) from about 0.10 to about 10.00 grams of spent hops; (b) from about 5 to about 1200 mg of 1,7-Bis(4-hydroxy-3-methoxyphenyl)hepta-1,6-diene-3,5-dione; (c) from about 0.10 to about 24 mg of zinc; and (d) from about 5 to about 1200 mg of 3-(2-(Decahydro-6-hydroxy-5-(hydroxymethyl)-5,8a-dimethyl-2-methylenenaphthyl)ethylidene)dihydro-4-hydroxyfuran-2(3H)-one.

8. The method according to claim 7, wherein the composition further comprises a compound selected from the group consisting of (4S,5S)-3,4-dihydroxy-4-[(1S)-hydroxy-4-methylpent-3-en-1-yl]-2-(3-methyl-butanoyl)-5-(3-methylbut-2-en-1-yl)cyclopent-2-en-1-one; (4R,5R)-3,4-dihydroxy-4-[(1R)-hydroxy-4-methylpent-3-en-1-yl]-2-(3-methyl-butanoyl)-5-(3-methylbut-2-en-1-yl)cyclopent-2-en-1-one; (4R,5R)-3,4-dihydroxy-4-[(1R)-hydroxy-4-methylpent-3-en-1-yl]-2-(2-methyl-butanoyl)-5-(3-methylbut-2-en-1-yl)cyclopent-2-en-1-one; (4R,5R)-3,4-dihydroxy-4-[(1R)-hydroxy-4-methylpent-3-en-1-yl]-5-(3-methyl-but-2-en-1-yl)-2-(2-methylpropanoyl)cyclopent-2-en-1-one; (4R,5R)-3,4-dihydroxy-4-[(1S)-hydroxy-4-methylpent-3-en-1-yl]-2-(3-methyl-butanoyl)-5-(3-methylbut-2-en-1-yl)cyclopent-2-en-1-one; (4R,5R)-3,4-dihydroxy-4-[(1S)-hydroxy-4-methylpent-3-en-1-yl]-2-(2-methyl-butanoyl)-5-(3-methylbut-2-en-1-yl)cyclopent-2-en-1-one; (4R,5R)-3,4-dihydroxy-4-[(1S)-hydroxy-4-methylpent-3-en-1-yl]-5-(3-methyl-but-2-en-1-yl)-2-(2-methylpropanoyl)cyclopent-2-en-1-one; (4R,5S)-3,4-dihydroxy-4-[(1R)-hydroxy-4-methylpent-3-en-1-yl]-2-(3-methyl-butanoyl)-5-(3-methylbut-2-en-1-yl)cyclopent-2-en-1-one; (4R,5S)-3,4-dihydroxy-4-[(1R)-hydroxy-4-methylpent-3-en-1-yl]-2-(2-methyl-butanoyl)-5-(3-methylbut-2-en-1-yl)cyclopent-2-en-1-one; (4R,5S)-3,4-dihydroxy-4-[(1R)-hydroxy-4-methylpent-3-en-1-yl]-5-(3-methyl-but-2-en-1-yl)-2-(2-methylpropanoyl)cyclopent-2-en-1-one; (4R,5S)-3,4-dihydroxy-4-[(1S)-hydroxy-4-methylpent-3-en-1-yl]-2-(3-methyl-butanoyl)-5-(3-methylbut-2-en-1-yl)cyclopent-2-en-1-one; (4R,5S)-3,4-dihydroxy-4-[(1S)-hydroxy-4-methylpent-3-en-1-yl]-2-(2-methyl-butanoyl)-5-(3-methylbut-2-en-1-yl)cyclopent-2-en-1-one; (4R,5S)-3,4-dihydroxy-4-[(1S)-hydroxy-4-methylpent-3-en-1-yl]-5-(3-methyl-but-2-en-1-yl)-2-(2-methylpropanoyl)cyclopent-2-en-1-one; (4S,5R)-3,4-dihydroxy-4-[(1R)-hydroxy-4-methylpent-3-en-1-yl]-2-(3-methyl-butanoyl)-5-(3-methylbut-2-en-1-yl)cyclopent-2-en-1-one; (4S,5R)-3,4-dihydroxy-4-[(1R)-hydroxy-4-methylpent-3-en-1-yl]-2-(2-methyl-butanoyl)-5-(3-methylbut-2-en-1-yl)cyclopent-2-en-1-one; (4S,5R)-3,4-dihydroxy-4-[(1R)-hydroxy-4-methylpent-3-en-1-yl]-5-(3-methyl-but-2-en-1-yl)-2-(2-methylpropanoyl)cyclopent-2-en-1-one; (4S,5R)-3,4-dihydroxy-4-[(1S)-hydroxy-4-methylpent-3-en-1-yl]-2-(3-methyl-butanoyl)-5-(3-methylbut-2-en-1-yl)cyclopent-2-en-1-one; (4S,5R)-3,4-dihydroxy-4-[(1S)-hydroxy-4-methylpent-3-en-1-yl]-2-(2-methyl-propanoyl)-5-(3-methylbut-2-en-1-yl)cyclopent-2-en-1-one; (4S,5R)-3,4-dihydroxy-4-[(1S)-hydroxy-4-methylpent-3-en-1-yl]-2-(2-methyl-butanoyl)-5-(3-methylbut-2-en-1-yl)cyclopent-2-en-1-one; (4S,5S)-3,4-dihydroxy-4-[(1R)-hydroxy-4- methylpent-3-en-1-yl]-2-(3-methyl-butanoyl)-5-(3-methylbut-2-en-1-yl)cyclopent-2-en-1-one; (4S,5S)-3,4-dihydroxy-4-[(1R)-hydroxy-4-methylpent-3-en-1-yl]-2-(2-methyl-butanoyl)-5-(3-methylbut-2-en-1-yl)cyclopent-2-en-1-one; (4S,5S)-3,4-dihydroxy-4-[(1R)-hydroxy-4-methylpent-3-en-1-yl]-5-(3-methyl-but-2-en-1-yl)-2-(2-methylpropanoyl)cyclopent-2-en-1-one; (4S,5S)-3,4-dihydroxy-4-[(1S)-hydroxy-4-methylpent-3-en-1-yl]-2-(2-methyl-butanoyl)-5-(3-methylbut-2-en-1-yl)cyclopent-2-en-1-one; and (4S,5S)-3,4-dihydroxy-4-[(1S)-hydroxy-4-methylpent-3-en-1-yl]-5-(3-methyl-but-2-en-1-yl)-2-(2-methylpropanoyl)cyclopent-2-en-1-one.

9. The method according to claim 7, wherein the composition further comprises a compound selected from the group consisting of (4R,5S)-3,4-dihydroxy-2-(3-methylbutanoyl)-5-(3-methylbutyl)-4-(4-methylpentanoyl)cyclopent-2-en-1-one; (4S,5S)-3,4-dihydroxy-2-(3-methylbutanoyl)-5-(3-methylbutyl)-4-(4-methylpentanoyl)cyclopent-2-en-1-one; (4S,5R)-3,4-dihydroxy-2-(3-methylbutanoyl)-5-(3-methylbutyl)-4-(4-methylpentanoyl)cyclopent-2-en-1-one; (4R,5R)-3,4-dihydroxy-2-(3-methylbutanoyl)-5-(3-methylbutyl)-4-(4-methylpentanoyl)cyclopent-2-en-1-one; (4R,5S)-3,4-dihydroxy-5-(3-methylbutyl)-4-(4-methylpentanoyl)-2-(3-methylpropanoyl)cyclopent-2-en-1-one; (4S,5S)-3,4-dihydroxy-5-(3-methylbutyl)-4-(4-methylpentanoyl)-2-(3-methylpropanoyl)cyclopent-2-en-1-one; (4S,5R)-3,4-dihydroxy-5-(3-methylbutyl)-4-(4-methylpentanoyl)-2-(3-methylpropanoyl)cyclopent-2-en-1-one; (4R,5R)-3,4-dihydroxy-5-(3-methylbutyl)-4-(4-methylpentanoyl)-2-(3-methylpropanoyl)cyclopent-2-en-1-one; (4R,5S)-3,4-dihydroxy-2-(2-methylbutanoyl)-5-(3-methylbutyl)-4-(4-methylpentanoyl)cyclopent-2-en-1-one; 5S)-3,4-dihydroxy-2-(2-methylbutanoyl)-5-(3-methylbutyl)-4-(4-methylpentanoyl)cyclopent-2-en-1-one; (4S,5R)-3,4-dihydroxy-2-(2-methylbutanoyl)-5-(3-methylbutyl)-4-(4-methylpentanoyl)cyclopent-2-en-1-one; and (4R,5R)-3,4-dihydroxy-2-(2-methylbutanoyl)-5-(3-methylbutyl)-4-(4-methylpentanoyl)cyclopent-2-en-1-one.

10. The method according to claim 7, wherein the composition further comprises a compound selected from the group consisting of (4S,5S)-3,4-dihydroxy-4-[(1S)-1-hydroxy-4-methylpentyl]-2-(3-methylbutano-yl)-5-(3-methylbutyl)cyclopent-2-en-1-one; 5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; (4S,5S)-3,4-dihydroxy-4-[(1S)-1-hydroxy-4-methylpentyl]-2-(3-methylbutanoyl)-5-(3-methylbutyl)cyclopent-2-en-1-one; and (4S,5S)-3,4-dihydroxy-4-[(1S)-1-hydroxy-4-methylpentyl]-2-(3-methylbutanoyl)-5-(3-methylbutyl)cyclopent-2-en-1-one.

11. The method according to claim 7, wherein the composition further comprises a pharmaceutically acceptable excipient selected from the group consisting of coatings, isotonic and absorption delaying agents, binders, adhesives, lubricants, disintergrants, coloring agents, flavoring agents, sweetening agents, absorbants, detergents, and emulsifying agents.

12. The method according to claim 7, wherein the composition further comprises one or more members selected from the group consisting of antioxidants, vitamins, minerals, proteins, fats, and carbohydrates.

* * * * *